US012661247B2

(12) United States Patent
Nia et al.

(10) Patent No.: US 12,661,247 B2
(45) Date of Patent: Jun. 23, 2026

(54) SELF-GROWING HEART VALVES

(71) Applicant: Edwards Lifesciences Corporation, Irvine, CA (US)

(72) Inventors: Nima V. Nia, Mission Viejo, CA (US); Hengchu Cao, Irvine, CA (US); Sakyasingh Tripathy, San Diego, CA (US); Douglas Thomas Dominick, Irvine, CA (US); Bingquan Su, Irvine, CA (US); Behnood Miri, Irvine, CA (US); Zahra Moyedi, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1125 days.

(21) Appl. No.: 17/485,239

(22) Filed: Sep. 24, 2021

(65) Prior Publication Data

US 2022/0008233 A1     Jan. 13, 2022

Related U.S. Application Data

(63) Continuation of application No. PCT/US2020/023274, filed on Mar. 18, 2020, which
(Continued)

(51) Int. Cl.
A61F 2/24 (2006.01)
A61F 2/90 (2013.01)
(Continued)

(52) U.S. Cl.
CPC ............... A61F 2/93 (2013.01); A61F 2/90 (2013.01); A61F 2/915 (2013.01); A61F 2002/825 (2013.01)

(58) Field of Classification Search
CPC ........ A61F 2/24; A61F 2/2409; A61F 2/2412; A61F 2/2415; A61F 2/2418;
(Continued)

(56) References Cited

U.S. PATENT DOCUMENTS 5,383,926 A * 1/1995 Lock .......................... A61F 2/92
606/198
5,907,893 A 6/1999 Zadno-Azizi et al.
(Continued)

FOREIGN PATENT DOCUMENTS

EP 1872743 B1 * 8/2009 ........... A61F 2/2418
FR 2788217 A1 * 7/2000 ........... A61F 2/2412
(Continued)

OTHER PUBLICATIONS

Forbes, et al., "Intravascular Stent Therapy for Coarctation of the Aorta", Methodist DeBakey cardiovascular journal, pp. 82-87, Apr. 2014, ResearchGate, Berlin, Germany.
(Continued)

*Primary Examiner* — Seema Mathew
(74) *Attorney, Agent, or Firm* — Chang and Hale LLP

(57) ABSTRACT

Described herein are artificial valves that have a frame and leaflets that grow or expand with a patient. Upon placing the valve inside the patient, the valve expands as the annulus of the patient expands. The frame of the valve is configured to expand which in turn causes the leaflets to expand (e.g., to grow). The valve includes a thin undulating wire embedded inside the leaflets. As the annulus of the patient grows, the frame expands, and as the frame expands, the leaflets grow. The growth or expansion of the leaflets is configured so that the valve continues to operate properly (e.g., the leaflets continue to coapt) with expansion of the annulus. The change in size of the valve can be configured to accommodate changes in size of the annulus from an infant or child to an adult.

20 Claims, 12 Drawing Sheets

Related U.S. Application Data is a continuation of application No. 16/686,673, filed on Nov. 18, 2019, now Pat. No. 11,559,415.

(60) Provisional application No. 62/823,901, filed on Mar. 26, 2019, provisional application No. 62/823,876, filed on Mar. 26, 2019.

(51) Int. Cl.

| | | |
|---|---|---|
| *A61F 2/915* | (2013.01) | |
| *A61F 2/93* | (2013.01) | |
| *A61F 2/82* | (2013.01) | |

(58) Field of Classification Search

CPC .. A61F 2/2463; A61F 2/243; A61F 2250/001; A61F 2250/0082; A61F 2/2427; A61F 2/02; A61F 2/246; A61F 2/07; A61F 2/475; A61F 2/821

See application file for complete search history.

(56) References Cited

U.S. PATENT DOCUMENTS

| | | | |
|---|---|---|---|
| 6,264,689 | B1 | 7/2001 | Colgan et al. |
| 6,579,314 | B1 | 6/2003 | Lombardi et al. |
| 9,119,714 | B2 | 9/2015 | Shandas et al. |
| 9,314,335 | B2 | 4/2016 | Konno |
| 9,375,310 | B2 | 6/2016 | Chung et al. |
| 9,381,103 | B2 * | 7/2016 | Abunassar ............. A61F 2/915 |
| 10,080,653 | B2 * | 9/2018 | Conklin ............... A61F 2/2409 |
| 10,543,085 | B2 * | 1/2020 | Chung ................. A61F 2/2445 |
| 10,702,407 | B1 * | 7/2020 | Armer .................... A61F 2/958 |
| 12,004,939 | B1 * | 6/2024 | Marshall ............... A61F 2/848 |
| 2002/0188348 | A1 | 12/2002 | DiMatteo et al. |
| 2003/0065386 | A1 * | 4/2003 | Weadock .................. A61F 2/07 623/2.38 |
| 2006/0235509 | A1 | 10/2006 | Lafontaine |
| 2007/0142907 | A1 * | 6/2007 | Moaddeb ............. A61F 2/2469 623/2.37 |
| 2007/0185571 | A1 * | 8/2007 | Kapadia .......... A61B 17/00234 623/2.11 |
| 2008/0004688 | A1 * | 1/2008 | Spenser ............... A61F 2/2418 623/2.14 |
| 2008/0004696 | A1 | 1/2008 | Vesely |
| 2008/0114452 | A1 * | 5/2008 | Gabbay ................. A61F 2/2412 623/2.17 |
| 2008/0140179 | A1 | 6/2008 | Ladisa |
| 2009/0099644 | A1 | 4/2009 | Biadillah et al. |
| 2010/0076548 | A1 * | 3/2010 | Konno ................. A61F 2/2409 623/2.11 |
| 2010/0076549 | A1 * | 3/2010 | Keidar ................. A61F 2/2466 623/2.36 |
| 2011/0160763 | A1 | 6/2011 | Ferrera et al. |
| 2012/0029624 | A1 | 2/2012 | Dierking et al. |
| 2012/0158125 | A1 * | 6/2012 | Obradovic ............... A61F 2/91 623/1.16 |
| 2012/0172980 | A1 * | 7/2012 | DuMontelle .......... A61F 2/2412 623/2.12 |
| 2012/0330413 | A1 | 12/2012 | Pavcnik |
| 2014/0188221 | A1 * | 7/2014 | Chung ................. A61F 2/2445 623/2.18 |
| 2015/0127082 | A1 | 5/2015 | Sudhir et al. |

| | | | |
|---|---|---|---|
| 2015/0366664 | A1 * | 12/2015 | Guttenberg ........... A61F 2/2418 623/2.17 |
| 2016/0008130 | A1 * | 1/2016 | Hasin .................... A61F 2/2466 623/2.37 |
| 2016/0015538 | A1 | 1/2016 | Kariniemi et al. |
| 2016/0213499 | A1 | 7/2016 | Zheng et al. |
| 2016/0220361 | A1 * | 8/2016 | Weber .................... A61L 27/18 |
| 2016/0302917 | A1 * | 10/2016 | Schewel .............. A61F 2/2445 |
| 2017/0000603 | A1 * | 1/2017 | Conklin .............. A61F 2/2409 |
| 2017/0000604 | A1 * | 1/2017 | Conklin .............. A61F 2/2409 |
| 2017/0014228 | A1 | 1/2017 | Emani et al. |
| 2017/0071732 | A1 * | 3/2017 | Conklin ............... A61F 2/2418 |
| 2017/0071735 | A1 * | 3/2017 | Guttenberg ........... A61F 2/2409 |
| 2018/0185144 | A1 | 7/2018 | Snyders |
| 2018/0289475 | A1 * | 10/2018 | Chung .................. A61F 2/2409 |
| 2019/0021854 | A1 * | 1/2019 | Conklin .............. A61F 2/2418 |
| 2019/0125517 | A1 * | 5/2019 | Cully ...................... A61F 2/958 |
| 2019/0209319 | A1 * | 7/2019 | Konno .................. A61F 2/2409 |
| 2020/0323633 | A1 * | 10/2020 | Conklin .............. A61F 2/2409 |
| 2021/0045872 | A1 * | 2/2021 | Kheradvar ......... A61M 25/1011 |
| 2021/0353408 | A1 * | 11/2021 | Chen ..................... A61F 2/2412 |
| 2022/0039945 | A1 * | 2/2022 | Guttenberg ........... A61F 2/2472 |
| 2023/0084393 | A1 * | 3/2023 | Pintor .................. A61F 2/2433 623/2.11 |
| 2023/0190462 | A1 * | 6/2023 | Nir ........................ A61F 2/2418 623/2.11 |
| 2023/0200986 | A1 * | 6/2023 | Chung ................. A61F 2/2418 623/1.13 |
| 2025/0161031 | A1 * | 5/2025 | Jin ........................ A61F 2/2409 |

FOREIGN PATENT DOCUMENTS

| | | | | |
|---|---|---|---|---|
| WO | | 0041652 | A1 | 7/2000 |
| WO | | 2012018779 | A2 | 2/2012 |
| WO | WO-2013019756 | A2 * | 2/2013 | .......... A61F 2/2475 |
| WO | WO-2018184225 | A1 * | 10/2018 | .......... A61F 2/2418 |
| WO | | 2019175889 | A1 | 9/2019 |
| WO | WO-2021061987 | A1 * | 4/2021 | .......... A61F 2/2418 |

OTHER PUBLICATIONS

Cabrera M.S, et al., "Understanding the Requirements of Self-expandable Stents for Heart Valve Replacement: Radial Force, Hoop Force and Equilibrium," Journal of the Mechanical Behavior of Biomedical Materials, Elsevier, Amsterdam, Netherlands, Feb. 7, 2017, vol. 68, pp. 252-264.

Nia N.V., et al., "Can a Self-Expanding Pediatric Stent Expand with an Artery? Relationship of Stent design to Vascular Biology," Catheterization and Cardiovascular Interventions, Cardiovascular Systems, Inc., Wiley, Hoboken, NJ, 2021, vol. 98, Issue. 1, pp. 1-9, (10 Pages).

Stoeckel D., et al., "Self-Expanding Nitinol Stents—Material and Design Considerations," Nitinol Devices & Components, European Radiology, Dec. 1, 2003, pp. 1-12 (13 Pages), [Retrieved on Jan. 17, 2022] Retrieved from URL.

Tyagi S., et aL, "Self-and Balloon-expandable Stent Implantation for Severe Native Coarctation of Aorta in Adults," American Heart Journal, Elsevier, Amsterdam, Netherlands, 2003, vol. 146, No. 5, pp. 920-928.

Stoeckel D., et al., "Self-expanding Nitinol Stents for the Treatment of Vascular Disease," Shape Memory Alloys for Biomedical Applications, Woodhead Publishing, 2009, pp. 237-256.

* cited by examiner

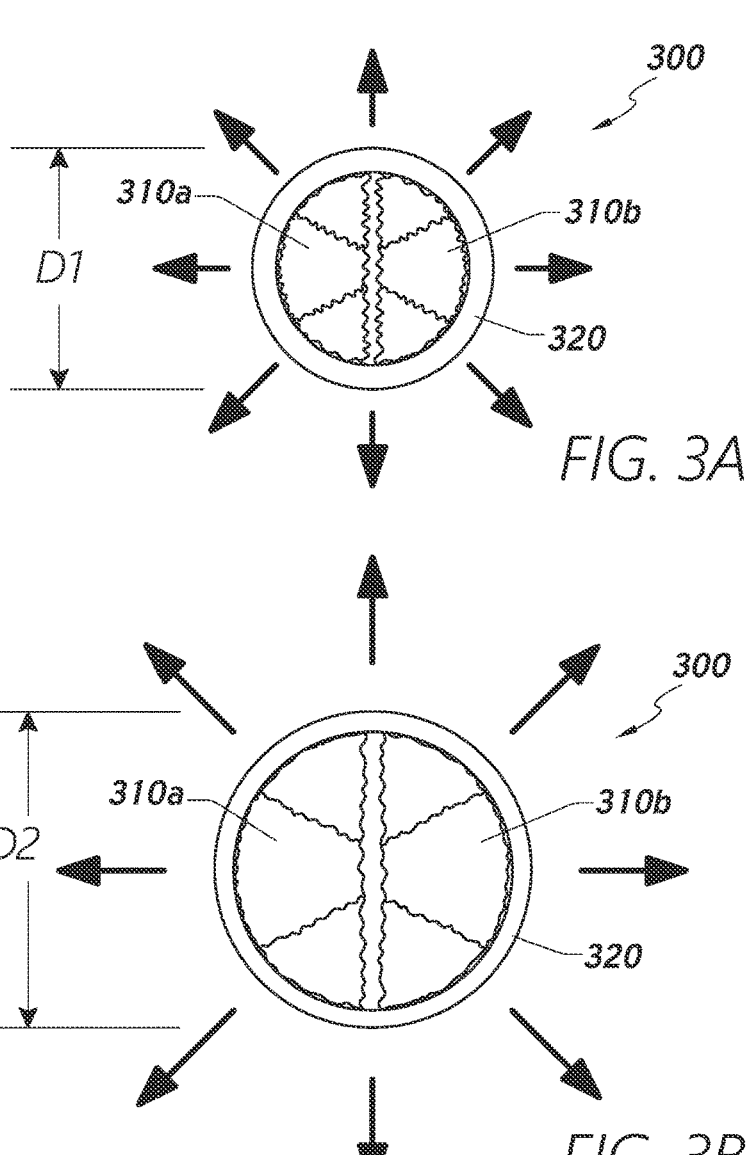
*FIG. 3A*
*FIG. 3B*
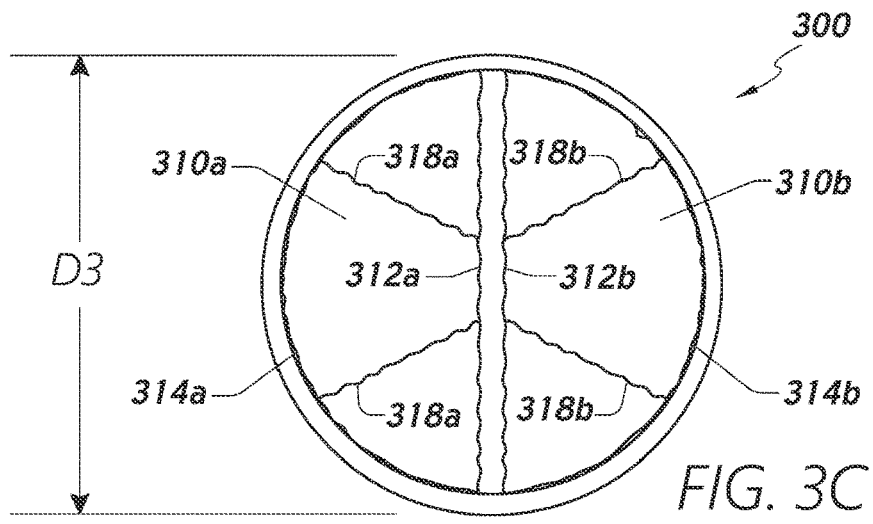
*FIG. 3C*

100

PROVIDE SELF-GROWING HEART VALVE DEVICE — 101

COMPRESS VALVE DEVICE TO LOW-PROFILE CONFIGURATION — 102

DISPOSE VALVE DEVICE IN DELIVERY SYSTEM — 103

DELIVER, IN CRIMPED STATE, SELF-GROWING VALVE DEVICE — 104

DEPLOY CRIMPED VALVE DEVICE IN NATIVE VALVE ANNULUS — 105

RELEASE VALVE DEVICE TO ALLOW VALVE DEVICE TO SELF-EXPAND AS PATIENT GROWS — 106

SELF-GROWING HEART VALVES

RELATED APPLICATIONS

This application is a continuation of International Patent Application Serial No. PCT/US2020/023274, filed Mar. 18, 2020 and entitled SELF GROWING HEART VALVES, which is a continuation of Utility patent application Ser. No. 16/686,673, filed Nov. 18, 2019 and entitled RADIALLY SELF-EXPANDING STENTS, which claims the benefit of U.S. Provisional Application No. 62/823,876, filed Mar. 26, 2019 and entitled SELF-GROWING HEART VALVES, and U.S. Provisional Application No. 62/823,901, filed Mar. 26, 2019 and entitled RADIALLY SELF-EXPANDING STENTS, the complete disclosures of all of which are hereby incorporated by reference in their entireties.

BACKGROUND

Field

The present disclosure relates to heart valves for heart valve replacement, and more particularly to the frame and leaflets that enable expansion of the heart valve with growth of the patient.

Description of Related Art

Congenital heart valve disease (CHVD) often involves pulmonary or aortic valves that do not form properly. CHVD can affect wide range of patients, from infants to the elderly, and represents a relatively large health care cost and risk. Patients with CVHD may have a heart valve with defective tissue leaflets that fail to properly coapt, the valve may be the wrong size or shape, or the valve may lack an opening through which blood can flow properly. Valve stenosis occurs when a valve does not open completely and thereby causes an obstruction of blood flow and can be fatal. Valve regurgitation occurs when the leaflets of the valve do not close completely thereby allowing blood to leak back into the prior chamber when the heart contracts. Surgery can be done to implant a biological or mechanical valve to replace a defective one.

SUMMARY

In a first aspect, the present disclosure provides an artificial heart valve that includes a frame configured to be secured to an annulus of a patient. The heart valve also includes a plurality of leaflets, individual leaflets having a peripheral edge operatively coupled to the frame and a coapting edge extending between ends of the peripheral edge, the peripheral edge and the coapting edge including an embedded support structure that expands with expansion of the frame and contracts with contraction of the frame. Expansion of the annulus of the patient causes the frame to expand which in turn cause the leaflets to grow to accommodate the larger size, the leaflets configured to remain capable of coapting with expansion of the annulus of the patient.

In some embodiments of the first aspect, there are three leaflets. In some embodiments of the first aspect, the frame is configured to expand from a size of less than or equal to 2 mm to greater than or equal to 21 mm. In some embodiments of the first aspect, the plurality of leaflets is configured to coapt for frame sizes between 2 mm and 21 mm.

In some embodiments of the first aspect, the embedded support structure comprises a nickel titanium alloy. In some embodiments of the first aspect, the embedded support structure comprises a coiled wire. In some embodiments of the first aspect, the embedded support structure comprises an undulating mesh.

In some embodiments of the first aspect, individual leaflets further include a bisecting support extending from the peripheral edge to the coapting edge. In further embodiments of the first aspect, the bisecting support includes a portion of the embedded support structure.

In some embodiments of the first aspect, the valve further includes a sealing member operatively coupled to an outer portion of the frame. In some embodiments of the first aspect, the heart valve is configured to replace an aortic valve of a child. In some embodiments of the first aspect, the heart valve is configured to replace a pulmonic valve of a child.

In some embodiments of the first aspect, expansion of the frame causes the peripheral edge of individual leaflets to expand circumferentially. In further embodiments of the first aspect, circumferential expansion of the peripheral edge of an individual leaflet results in expansion of the corresponding coaptation edge of the individual leaflet. In further embodiments of the first aspect, the expansion of the coaptation edge of the individual leaflet does not prevent the corresponding coaptation edges from coapting.

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

FIGS. 3A, 3B, and 3C illustrate a plan view of an example valve as it expands to accommodate a growing patient.

3

Figure 9:
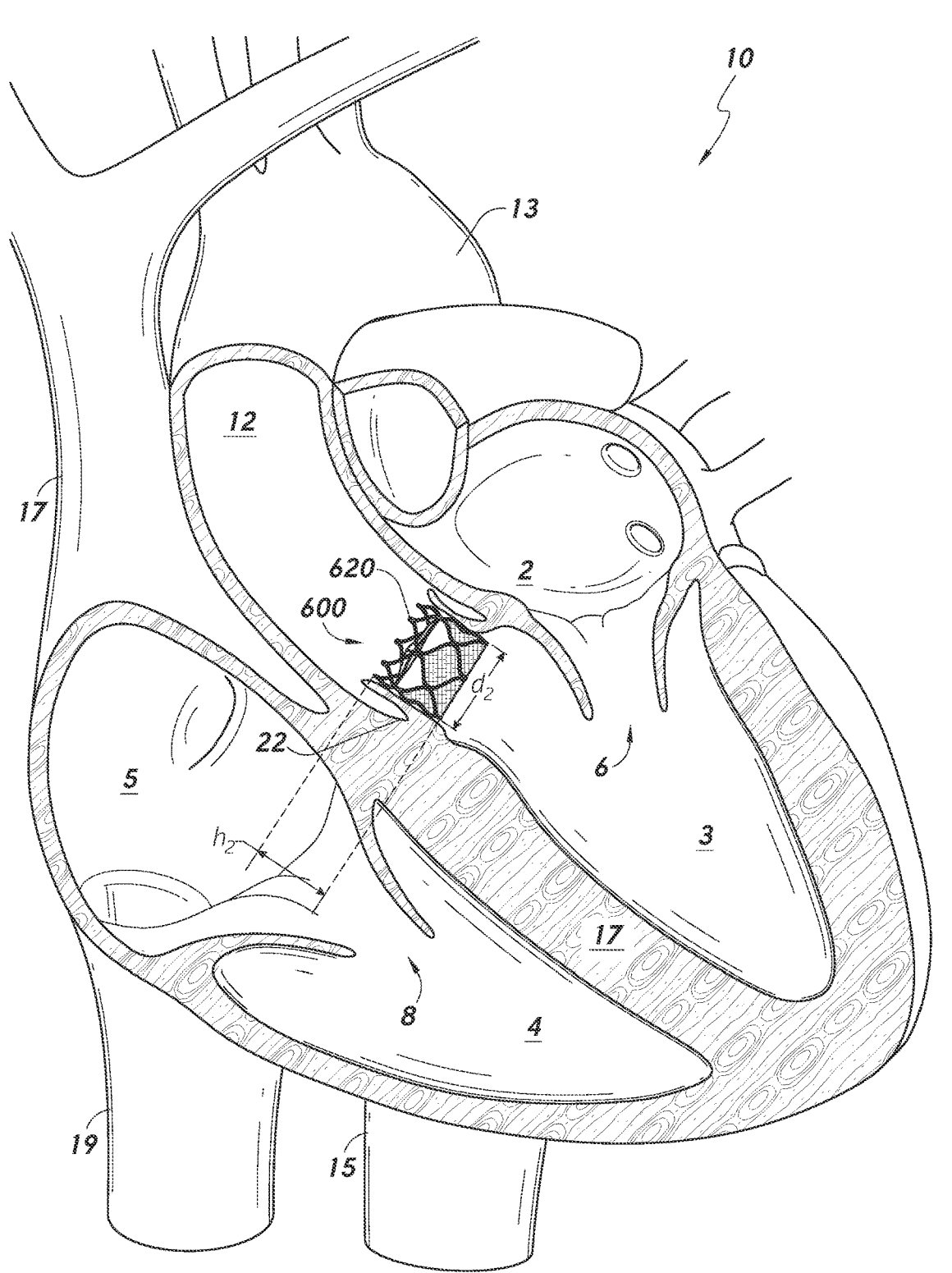

FIG. 9 shows a radially self-expanding heart valve device implanted in cardiac anatomy in a growth-expansion configuration in accordance with one or more embodiments.

Figure 10:
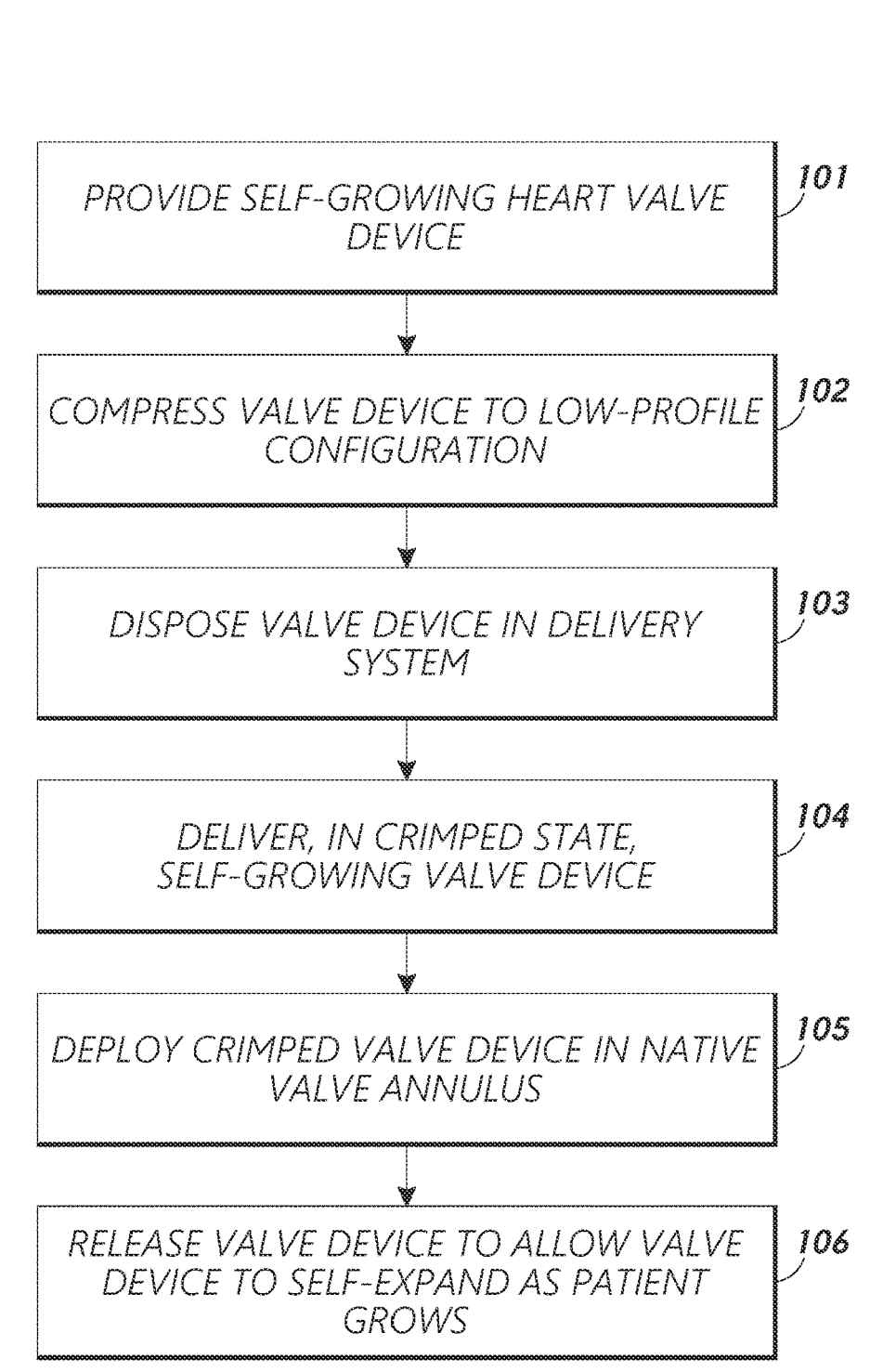

FIG. 10 illustrates a flow diagram of an example method for treating heart valve disease with any of the radially self-expanding heart valve devices described herein.

Figure 11A:
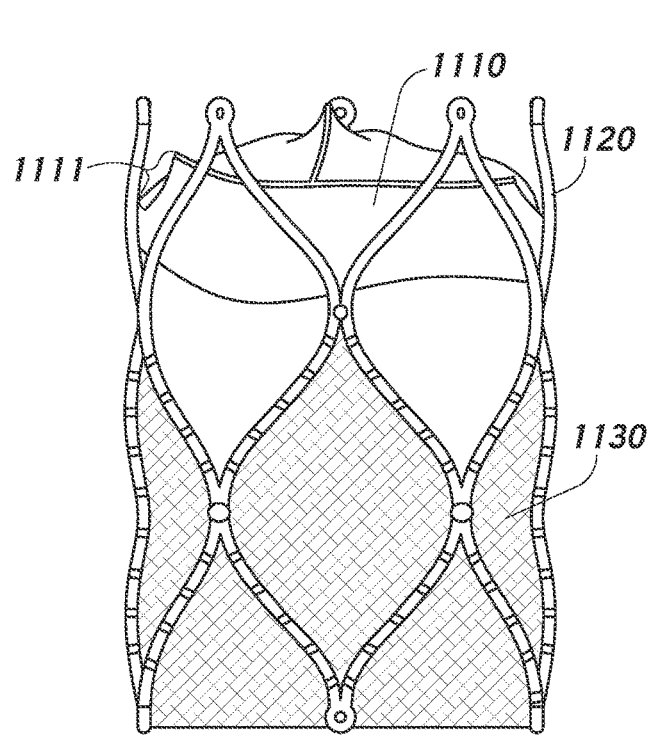
Figure 11B:
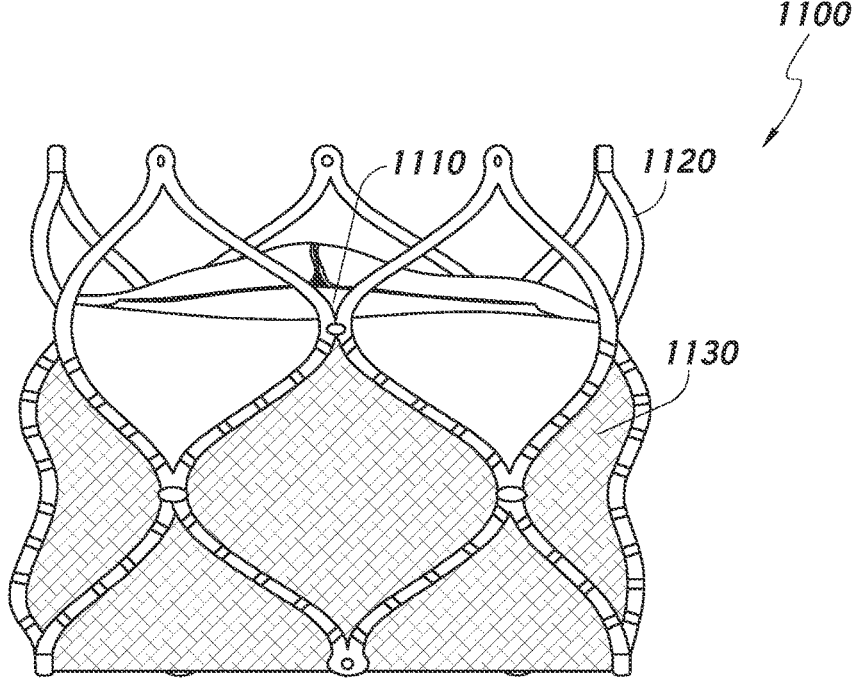

FIGS. 11A and 11B show perspective views of a self-growing heart valve device in partially- and fully-expanded states, respectively, in accordance with one or more embodiments.

DETAILED DESCRIPTION OF SOME EMBODIMENTS

The headings provided herein, if any, are for convenience only and do not necessarily affect the scope or meaning of the claimed invention.

Overview

The heart is a hollow muscular organ having four pumping chambers separated by four heart valves, namely the aortic, mitral (or bicuspid), tricuspid, and pulmonary valves. Each heart valve comprises a relatively dense fibrous ring known as the annulus, and two or more leaflets or cusps attached to the annulus. Congenital heart valve disease (CVHD) typically affects the aortic or pulmonary valves, which may be improperly formed in some instances. Such malformation may include, for example, tissue flaps that do not coapt, valve features that are the wrong size or shape, or valves that lack a suitable opening for blood flow (e.g., valve stenosis). CHVD can affect infants, children, adolescents, and adults.

To address CHVD and other heart valve diseases, some solutions involve the replacement of the malformed or defective heart valve with a prosthetic heart valve device. In traditional valve replacement operations, the damaged native valve leaflets may be excised, and the annulus may be sculpted to receive a replacement prosthetic valve. In some implementations, the native valve leaflets may be simply pushed aside by the frame of the prosthetic valve implant device.

When a replacement valve is implanted in an infant, child, or adolescent, the replacement valve may become too small over time as the patient grows. If this occurs, additional surgery may be required to implant a larger prosthetic valve suited to the patient. This may occur multiple times over the lifetime of the patient. For a patient and their family, each additional surgery increases the associated risks, dangers, costs, and emotional stress. For example, surgical aortic valve replacement can be associated with one or more of the following complications, issues, and/or risks: general risks associated with open heart surgery, the lack of suitable available pediatric heart valve devices, requirement of future replacement of a placed valve device, stenosis, which can make further surgery likely or inevitable, aneurysm formation/development, and tears in one or more portions of the aortic anatomy. Notably, appropriate prosthetic heart valve devices for patients that weigh less than about 10 kg (e.g., infants, babies, and toddlers) can be lacking. Furthermore, due to tissue growth, deformation, and/or other environmental factors, valve implant devices implanted within the aortic valve annulus or other anatomy can become dislodged and/or migrate or shift from their desired target position, orientation, and/or location post-operatively over time due to growth of the implantation vessel/anatomy.

Accordingly, to address these and other issues, disclosed herein are artificial prosthetic valve devices that include a frame and/or leaflets that are configured to grow or expand with the growth of the patient. Upon placing a heart valve device of the present disclosure inside the patient, the valve may be configured to expand as the annulus of the patient expands, thereby reducing or eliminating the need for future surgeries for children with CVHD. For example, the frame of the valve can be configured to expand, which may in turn advantageously cause expandable leaflets that are indirectly or directly coupled to the frame to expand (e.g., to grow). The terms "coupled" and "coupling" are used herein according to their broad and ordinary meanings. For example, where a first feature, element, component, device, or member, is described as being "coupled" with or to a second feature, element, component, device, or member, such description may be understood as indicating that the first feature, element, component, device, or member, or portion thereof, is physically/mechanically attached, fixed, fastened, mounted, connected, linked, or joined to, or united, associated together, or integrated with, or embedded at least partially within, or otherwise physically related to, the second feature, element, component, device, or member, or portion thereof, whether directly or indirectly. A "coupling" can refer to any device, structure, form, tool, mechanism, means, position, apparatus, or portion, component, or position thereof that at least partially facilitates and/or effects/ achieves the coupling of two or more features, elements, components, devices, or members, and/or portions thereof.

In some embodiments, heart valve devices include one or more thin undulating (e.g., zigzag, sinusoidal, ruffled, etc.) or coiled wires embedded inside one or more portions of the device, such as the leaflet(s). For example, as the annulus of the patient grows, the frame of the prosthetic valve device can expand automatically in turn, whereas as the frame expands, the leaflets may be inclined to grow along with the frame. The growth or expansion of the leaflets can be configured so that the valve continues to operate properly (e.g., the leaflets continue to coapt) with expansion of the annulus. The range of operational sizes of the valve device can accommodate changes in size of the annulus as a patient grows from an infant or child to an adult. Advantageously, the disclosed self-growing valve devices can reduce or eliminate the likelihood of future surgical procedures to implant larger artificial valves with patient growth. Advantages of aspects of the present disclosure can also include a reduction of lifestyle changes, emotional stress, uncertainties for families, and health care costs.

As referenced above, in addition to self-expanding valve leaflets, heart valve devices of the present disclosure can include self-expanding and/or expandable frames to which the leaflets are directly or indirectly attached/secured. For example, expanding heart valve devices of the present disclosure can include frame components that advantageously open-up or widen with the growth of the aorta 12 and/or aortic valve annulus 22 (see FIG. 1). Certain of the disclosed devices include heart valve frames that are advantageously configured to produce an outward radial force on the aortic annulus and/or conduit anatomy. The radial force produced by the frame can serve to cause continued expansion of the frame in accordance with the growth of the anatomy in which it is implanted. Furthermore, certain of the disclosed heart valve frames can be radially crimped/compressed to relatively small sizes/diameters for placement in anatomy of relatively small patients (e.g., less than about 10 kg in size) and can be configured to expand to widen the aorta and/or aortic valve annulus and to accommodate growth in the patient. Advantageously, this functionality can reduce the incidences of and/or need for lifestyle changes, emotional stress, uncertainties for families, additional surgical procedures, and/or health care costs.

The terms "crimped" and "compressed" configurations and states of heart valve devices and valve frames are used according to their broad and ordinary meanings and refer to a configuration or state of a valve device/frame having a lowest or substantially-lowest diametrical profile for the valve frame, or a state or configuration that is in accordance with a delivery profile for transportation within a delivery catheter or sheath. The terms "expanded" and "initial expanded" state and configuration are used according to their broad and ordinary meanings and refer to a configuration or state of a self-expanding valve device/frame having a diameter near or equal to that of a target blood vessel (e.g., aortic arch and/or descending aorta of a child or infant) at or immediately after implantation of the valve frame therein. The terms "growth-expansion," "further-expanded," and "post-operative expansion" configuration and state are used herein according to their broad and ordinary meanings and refer to a state or configuration of a radially self-growing/ expanding valve device/frame having a diameter greater than that of the valve frame at or soon after implantation thereof, wherein such diameter expansion is produced or effected at least in part by outward radial force exerted inherently by the valve frame structure and/or fixation to a vessel/annulus that undergoes diametrical growth over a post-operative/implantation period of time. Therefore, radially self-expanding valve devices/frames in accordance with embodiments of the present disclosure can be considered to be in a growth-expansion or post-implantation-expansion state a growth period of time after implantation in which the diameter of the valve device/frame has increased without requiring a post-implantation intervention to achieve or effect such expansion.

It is to be understood that although certain self-growing heart valve devices described herein are described as being used to treat aortic congenital heart valve disease, the disclosed devices can be used in a number of different applications, including treatment of pulmonary valve disease, mitral valve disease, and tricuspid valve disease.

Figure 1:
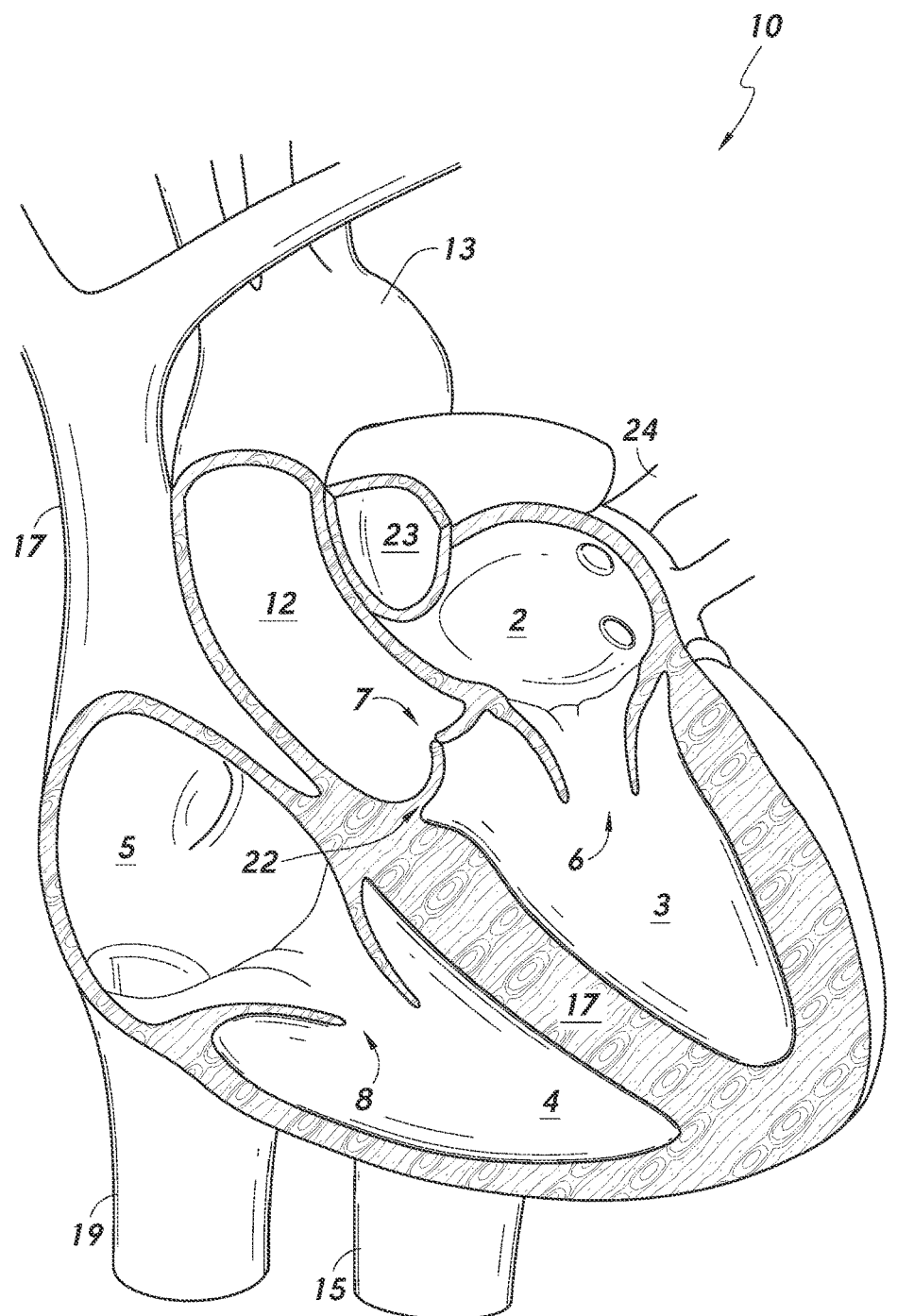
FIG. 1 illustrates a cut-away anterior view of a heart, showing the internal chambers, valves and adjacent structures.

The following includes a general description of human cardiac anatomy that is relevant to certain inventive features and embodiments disclosed herein and is included to provide context for certain aspects of the present disclosure. As illustrated in FIG. 1, the human heart 10 has four chambers, which include two upper chambers denoted as atria 2, 5 and two lower chambers denoted as ventricles 3, 4. A septum 17 divides the heart 10 and separates the left atrium 2 and left ventricle 3 from the right atrium 5 and right ventricle 4. The heart further contains four valves 6, 7, 8 (pulmonary valve not shown for visual clarity). The valves generally function to maintain the pressure and unidirectional flow of blood through the body and to prevent blood from leaking back into a chamber from which it has been pumped.

Although emphasis is placed on replacement of the aortic valve, the valves disclosed herein can be configured to replace any of the valves of the heart 10. Two valves separate the atria 2, 5 from the ventricles 3, 4, denoted as atrioventricular valves. The mitral valve 6, also known as the left atrioventricular valve, controls the passage of oxygenated blood from the left atrium 2 to the left ventricle 3. The aortic valve 7 separates the left ventricle 3 from the aortic artery (aorta) 12, which delivers oxygenated blood via the circulation to the entire body. The aortic valve 7 and mitral valve 6 are part of the left heart, which controls the flow of oxygen-rich blood from the lungs to the body. The right atrioventricular valve, the tricuspid valve 8, controls passage of deoxygenated blood into the right ventricle 4 from the right atrium 5.

The pulmonary valve (not shown) separates the right ventricle 4 from the pulmonary artery 23. The right ventricle 4 pumps deoxygenated blood through the pulmonary artery 23 to the lungs wherein the blood is oxygenated and then delivered to the left atrium 2 via the pulmonary veins 24. Accordingly, the tricuspid valve 8 and pulmonic valve are part of the right heart, which control the flow of oxygen-depleted blood from the body to the lungs. The aortic valve 7 and pulmonary valve have three cusps, or leaflets, that open and close and thereby function to prevent blood from leaking back into the ventricles after being ejected into the pulmonary artery 23 or aorta 12 for circulation. The mitral valve 6 and tricuspid valve 8 include two or more cusps, or leaflets, that are encircled by a variably dense fibrous ring of tissues known as the annulus. The valves are anchored to the walls of the ventricles by chordae tendineae (not shown). The chordae tendineae are cord-like tendons that connect the papillary muscles (not shown) to the leaflets of the mitral valve 6 and tricuspid valve 8, respectively.

With further reference to the aortic anatomy of the heart 10, the ascending aorta 12 generally begins at the opening of the aortic valve 7 in the left ventricle 3 of the heart. The ascending aorta 12 can run through a common pericardial sheath with the pulmonary trunk 23. At the root of the ascending aorta 12, the blood vessel lumen may generally present three relatively small pockets (i.e., aortic sinuses, or "sinuses of Valsalva") between the cusps of the aortic valve 7 and the wall of the aorta 12. The left aortic sinus (not shown) contains the origin of the left coronary artery and the right aortic sinus (not shown) likewise gives rise to the right coronary artery. The posterior aortic sinus (not shown) does not give rise to a coronary artery.

The aortic arch 13 loops over the left pulmonary artery 23 and the bifurcation of the pulmonary trunk. The transition from the ascending aorta 12 to the aortic arch 13 may be considered to be at or near the pericardial reflection on the aorta. The aortic arch 13 has three major branches, including the brachiocephalic trunk, the left common carotid artery, and the left subclavian artery. The brachiocephalic trunk supplies the right side of the head and neck as well as the right arm and chest wall, while the latter two together supply the left side of the same regions. The aortic arch 13 transitions to the descending thoracic aorta, which runs generally from the heart 10 to the diaphragm (not shown). The descending thoracic aorta transitions to the abdominal aorta 15, which gives rise to lumbar and musculophrenic arteries, renal and middle suprarenal arteries, and/or visceral arteries (none of which are shown in FIG. 1 for simplicity).

Figure 2B:
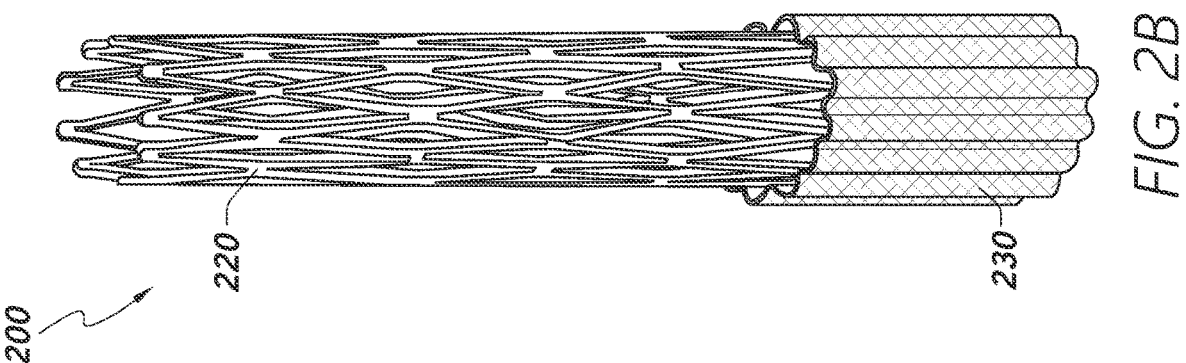
FIGS. 2A and 2B illustrate an example replacement valve in an expanded state and a compact state.
Figure 2A:
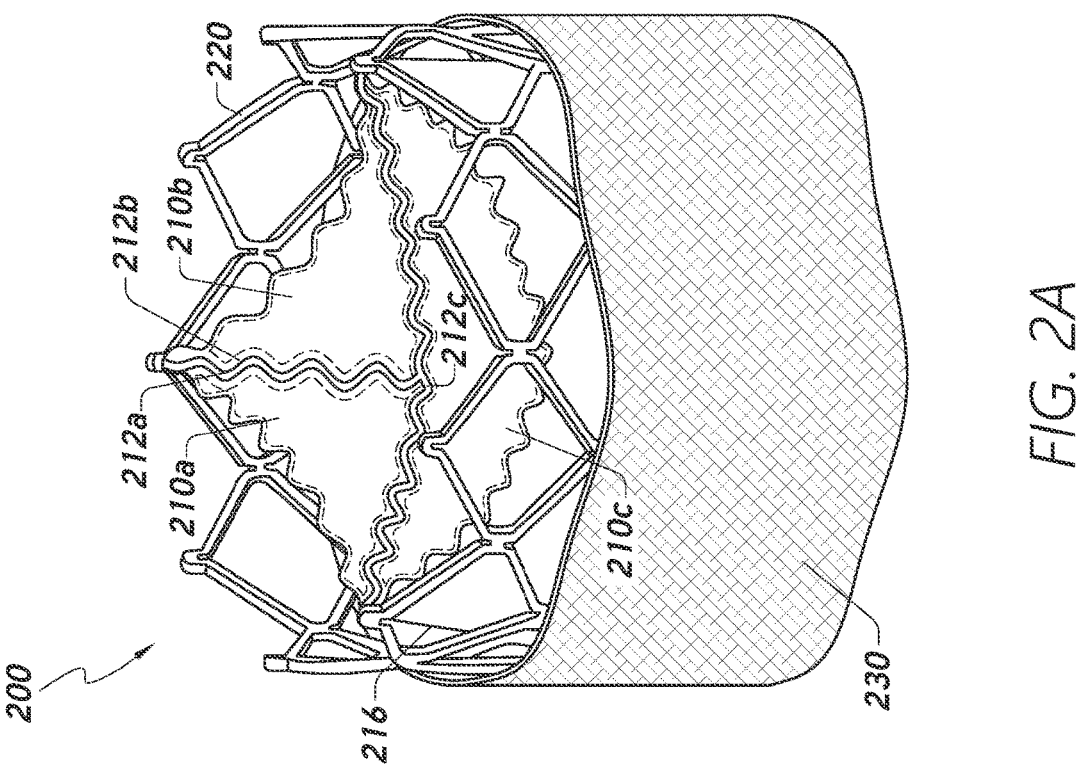

FIGS. 2A and 2B illustrate an example replacement valve device 200 in a fully expanded state in FIG. 2A and a compressed/compact state in FIG. 2B. The valve 200 is configured to be operable between the compressed state and the expanded state by employing leaflets 210a-210c that expand with an expandable frame 220 in such a way that the leaflets 210a-210c coapt at substantially all sizes between the compact state and the expanded state. To enable coaptation of the leaflets 210a-210c throughout the range of sizes of the valve, the leaflets 210a-210c include a structural support, such as one or more embedded wires or an embedded mesh, that provides suitable structure to the leaflets at a range of sizes. In some embodiments, the structural support includes one or more undulating (e.g., zig zag, sinusoidal, etc.) wires made of an alloy such as nickel titanium. The structural support can be along a peripheral edge of the leaflet(s) 210a-210c and/or along a coaptation edge 212a-212c of the leaflet(s) 210a-210c. In some embodiments, the leaflets 210a-210c can include one or more bisecting supports as part of the structural support, wherein a bisecting support runs from a peripheral edge to a coaptation edge of a leaflet.

The prosthetic valve 200 forms a conduit having an inlet end and an outlet and is made of pliant material arranged so to present collapsible walls at the outlet. The valve assembly is mounted on a support structure or frame 220 such as a stent adapted to be positioned at a target location within the body duct. The frame 220 comprises a net-like configuration designed to be adapted to crimp evenly so as to present a narrow configuration or compact configuration for operation in the vasculature of a small patient (e.g., a child or an infant) and to expand to occupy the passage at the target location as the patient grows. The prosthetic valve 200 includes a sealing device or component 230 (also referred to as a sealing member, or skirt) mounted (e.g., stitched) to the frame. The prosthetic valve 200 also includes a valvular structure, including multiple (e.g., three) leaflets 210a-210c mounted/coupled to the frame 220 to permit flow through the valve 200 in the normal direction of blood flow and block the flow of blood in the opposite direction. The sealing device 230 can be in the form of an annular skirt positioned inside and/or outside of the frame 220. The prosthetic valve 200 is adapted to be deployed in the native aortic or pulmonic annulus, although it may also be adapted to replace the other native valves of the heart, such as the mitral valve or the tricuspid valve.

The frame 220 can be made of any of various suitable plastically-expandable materials (e.g., stainless steel, etc.) or self-expanding materials (e.g., Nitinol) as known in the art. When constructed of a plastically-expandable material, the frame 220 (and thus the prosthetic valve 200) can be crimped to a radially compressed state on a delivery catheter and then expanded inside a patient by an inflatable balloon or equivalent expansion mechanism. When constructed of a self-expandable material, the frame 220 (and thus the prosthetic valve 200) can be crimped to a radially compressed state and restrained in the compressed state by insertion into a sheath or equivalent mechanism of a delivery catheter. Once inside the body, the valve can be advanced from the delivery sheath, which allows the prosthetic valve to expand to be implanted at the targeted site.

The valve leaflet assembly can be made from biological matter, such as a natural tissue, pericardial tissue or other biological tissue. Alternatively, the valve leaflets may be made from biocompatible polymers or similar materials. The frame 220 can be made from shape memory alloys such as nickel titanium (nickel titanium shape memory alloys, or NiTi, as marketed, for example, under the brand name Nitinol), or other biocompatible metals. Likewise, suitable plastically-expandable materials that can be used to form the frame 220 include, without limitation, stainless steel, a nickel-based alloy (e.g., a nickel-cobalt-chromium alloy), polymers, or combinations thereof. In particular embodiments, frame 220 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. The sealing component/device 230 desirably comprises a thin, flexible sheet of material, and can be made of any of various suitable materials, such as a fabric (e.g., polyethylene terephthalate (PET) (sold under the tradename Dacron®), ultra-high molecular weight polyethylene (UHMWPE) (sold under the tradename Dyneema Purity®), etc.), tissue (e.g., pericardial tissue), metal, sponge, or polymer.

The frame 220 is preferably annular, but may be provided in other shapes too, depending on the cross-section shape of the desired target location passage. Individual leaflets 210a-210c can be sutured to the frame 220 using conventional techniques and/or mechanisms, such as sewing it to several anchoring points on the frame 220, or riveting it, pinning it, adhering it, or welding it, or use any other suitable way of attachment.

The entire valve structure 200 can be adapted to be radially crimped and radially expanded, which may provide ease of navigation through narrow passages in the vasculature during positioning of the device and adequate deployment on the final location. In addition, the ability to crimp the device 200 to a sufficiently small diameter, as described in detail herein, can provide operability at a range of sizes so that the valve 200 continues to properly coapt as the patient grows. In some embodiments, the valve 200 does not experience relative movement between the leaflet assembly and support beams of the frame 220 (e.g., along the longitudinal central axis of the device) to enable operability at a range of radial sizes.

Figure 2C:
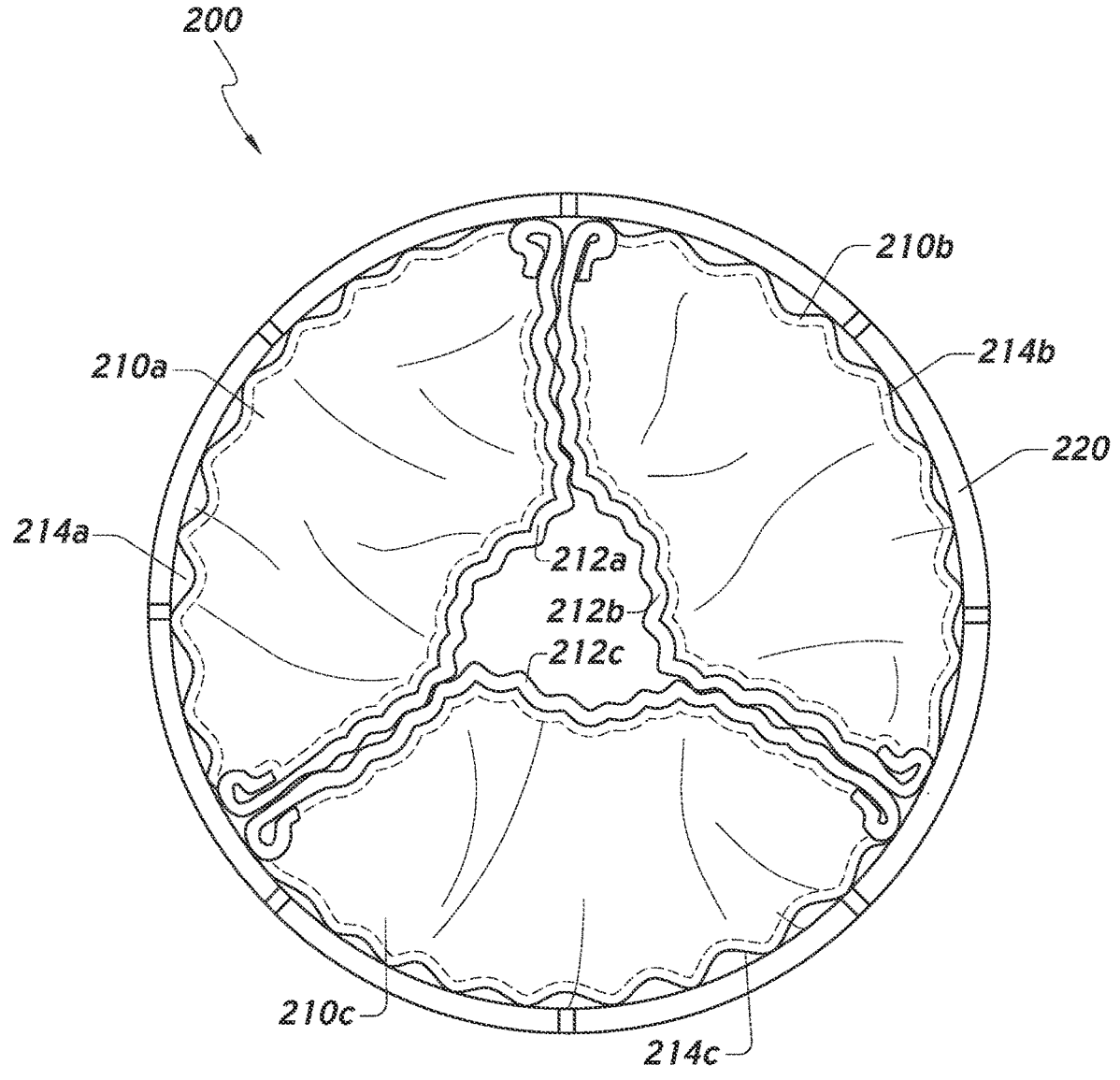
FIG. 2C illustrates a top view of the example valve of FIGS. 2A and 2B in a state between the fully expanded state and the compact state.

FIG. 2C illustrates a top view of the example valve 200 of FIGS. 2A and 2B in a state between the fully expanded state and the compact state. The top view better illustrates the leaflets 210a-210c, which can be formed of any suitable expandable, biocompatible material such as, for example and without limitation, expandable polymers, pericardial tissue (e.g., bovine pericardial tissue), biocompatible synthetic materials, or various other suitable natural or synthetic materials as known in the art and described in U.S. Pat. No. 6,730,118, which is incorporated by reference herein. Within the material of the leaflets 210a-210c, a support structure can be embedded that enables expansion of the leaflets 210a-210c in a targeted way that preserves operability (e.g., the ability to coapt) over a range of sizes of the valve 200. The support structure can be an embedded wire or wires and/or an embedded mesh structure. As the frame 220 expands, points along a peripheral edge 214a-214c of a leaflet 210a-210c are pulled apart axially (e.g., circumferentially with respect to the shape of the frame 220; the distance between points on the periphery of the leaflets increases), which causes the embedded support structure to expand along the coaptation edges 212a-212b and/or other bisecting supports to enable expansion of the leaflets 210a-210c with expansion of the frame 220.

In a more compact state, the valve 200 is operable or functional (e.g., the leaflets 210a-210c generally coapt) due at least in part to redundancy on the leaflets 210a-210c. In other words, the undulating coaptation edges 212a-212c overlap sufficiently to coapt properly in a compact state. In an expanded state, the valve 200 remains operable or functional due at least in part to the coaptation edges 212a-212c being aligned so that they come together to coapt. Thus, the valve 200 is configured to be suitable for pediatric use as well as for adult use and to be operable as a patient grows from an infant to an adult. The valve 200 can be configured to be crimped to a relatively small size for delivery and to be implanted and to operate in a range of sizes. For example, the valve 200 can operate (e.g., properly be implanted and regulate blood flow) with a radial size less than or equal to about 2 mm up to a radial size that is at least about 21 mm. The valve 200 includes the frame 220 that is configured to be secured to an annulus of a patient. The valve 200 also includes leaflets 210a-210c that individually include undulating or coiled self-expanding wire embedded within the leaflets 210a-210c (e.g., at or near the dashed lines shown in FIGS. 2A and 2C. Expansion of the annulus of the patient causes the frame 220 to expand which in turn causes the leaflets 210a-210c to grow to accommodate the larger size. As the frame 220 expands, the leaflets 210a-210c are configured to remain capable of coapting with expansion of the annulus of the patient.

The frame 220, as well as other heart valve frame solutions in accordance with embodiments of the present disclosure, can be self-expanding in that they may be configured to operate (e.g., to apply an outward radial force and/or to resist an inward radial force of the target vessel) between a relatively crimped or compact state and an expanded state. In some embodiments, the disclosed valve frames can have an initial crimped/compact delivery state and post-implantation expanded state, respectively, with respective diameters that are less than or equal to about 6 mm and/or greater than or equal to about 10 mm, less than or equal to about 4 mm and/or greater than or equal to about 15 mm, or less than or equal to about 2 mm and/or greater than or equal to about 20 mm. In some embodiments, the disclosed stents can operate with a height that ranges from between less than or equal to about 14 mm and/or greater than or equal to about 20 mm, less than or equal to about 10 mm and/or greater than or equal to about 25 mm, or less than or equal to about 20 mm and/or greater than or equal to about 42 mm. In a crimped state, the disclosed valve frames can be configured to be deliverable in a small delivery system (e.g., less than or equal to about 5-6 French). It should be understood that these numerical values are provided as examples only, and any other numbers producing the disclosed radial-expansion functionality would also fall within the scope of the present disclosure.

The disclosed valve frames can be configured to produce sufficient radial force to resist elastic recoil for relatively tight aortic anatomy (e.g., annulus, artery). Valve frames in accordance with embodiments of the present disclosure can be configured so that when implanted in a patient, the patient's inflammatory response does not cause significant stenosis, restenosis, or aneurysm. Furthermore, the disclosed valve frames can be resistant to downstream embolization. The disclosed valve frames can be configured with nominal calibers suitable for common lesions. In some embodiments, the radial hoop strength of valve frames in accordance with embodiments of the present disclosure can be similar to balloon-expandable valve frames, such as the PALMAZ GENESIS® manufactured by CORDIS®, or the like. In certain implementations, the disclosed valve frames can be configured to be relatively conspicuous under applicable image-guidance modalities, such as magnetic resonance imaging, sonic/echo imaging, and/or the like. In some embodiments, the disclosed valve frames can be configured to provide relatively high radial force sufficient to overcome immediate recoil with respect to the intended applications.

In some embodiments, valve frame devices in accordance with the present disclosure are configured to have/provide sufficient radial strength to withstand relevant structural loads, such as radial compressive forces imposed on the valve frame by the annulus and/or walls of a vessel as it resides in such anatomy. Radial strength, which should be understood to refer to the ability of a valve frame to resist radial compressive forces, relates to a valve frame's radial yield strength and radial stiffness around a circumferential direction of the valve frame. The configuration of the struts, joints, and nodes can be tailored to achieve sufficient or targeted ranges of radial strength to widen a narrowed vessel and to maintain the widened vessel at a targeted size.

The sizes of the disclosed valve frames can be suitable for implantation in some human children, including children that are less than about 10 kg. The diameter of the aorta in a person typically decreases moving from the aortic sinus just above the aortic valve to the thoracoabdominal aorta at the level of the diaphragm. Typical diameters of aortas in children weighing about 12 kg can be about 14 mm at the aortic sinus and about 7 mm at the level of the diaphragm. Children weighing less than about 12 kg can have aortic diameters that are less than these numbers. The internal diameter of the aortic ostium can generally be linearly correlated with body length. Furthermore, studies have been conducted measuring aortic diameters for infants and children with results indicating the linear relationship between body length and aortic diameters, where an increase in body length from 30 cm to 140 cm corresponded to a linear change in the internal diameter of the aortic ostium of the ascending aorta from about 4.5 mm to about 19.5 mm. Thus, the disclosed self-growing heart valve devices can advantageously be configured to function over a diameter range from about 2 mm to about 20 mm, allowing the disclosed valve devices to be used in patients that weigh less than or equal to about 10 kg.

FIGS. 3A, 3B, and 3C illustrate a plan view of an example valve 300 as it expands to accommodate a growing patient. FIG. 3A illustrates the valve 300 in a compact state suitable for an infant or child. FIG. 3B illustrates the valve 300 in a mid-range state suitable for a child or adolescent. FIG. 3C illustrates the valve 300 in an expanded state suitable for an adult. As stated herein, the disclosed valves are typically configured to include three leaflets to replace aortic and/or pulmonic valves, however, the valve 300 is illustrated to include two leaflets to better illustrate certain elements of the valve 300 and to provide support for expandable or self-growing valves with two leaflets.

The frame 320 expands from a diameter D1 to a diameter D3, where diameter D1 can be less than or equal to about 2 mm and the diameter D3 can be at least about 21 mm. The diameter D2 is greater than D1 and less than D3. For each diameter D1, D2, D3, the leaflets 310a, 310b are configured to coapt properly to prevent the backflow of blood or regurgitation and to open to allow forward flow of blood. The leaflets 310a, 310b each include a two bisecting supports 318a, 318b that extend from a peripheral edge 314a, 314b to a coaptation or free edge 312a, 312b. The bisecting supports 318a, 318b can be embedded within the leaflets 318a, 318b for structural purposes to improve strength, to reinforce the leaflets 310a, 310b, and/or to squeeze and to expand the leaflets 310a, 310b in response to the frame squeezing or expanding radially in size.

The peripheral edges 314a, 314b, the coaptation or free edges 312a, 312b, and the bisecting supports 318a, 318b can each include support structures embedded within the material of the leaflets 310a, 310b. By way of example, the support structure of one or more of these features can include zig zag mesh or wires. The mesh or wires can be made of metals, polymers, or other suitable materials. In some embodiments, the support structure can be made of a self-expanding material such as a nickel titanium alloy, examples of which have been described herein.

As the frame 320 expands (as indicated by the arrows pointing radially outward), points on the peripheral edges 312a, 312b that are anchored to the frame 320 are stretched apart. This causes the support structure within these edges and/or within the material of the leaflets 310a, 310b to flatten or uncoil, also affecting the support structure of the bisecting supports 318*a*, 318*b* and the coaptation edges 312*a*, 312*b*. This results in the leaflet 310*a*, 310*b* expanding and flattening with expansion of the frame 320.

Figure 4A:
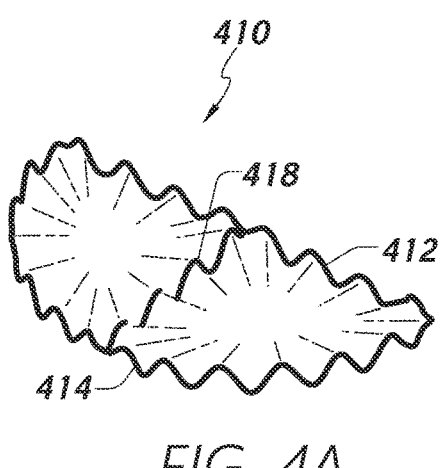
FIGS. 4A, 4B, 4C, 4D, and 4E illustrate an example leaflet of a valve as it grows or expands.
Figure 4B:
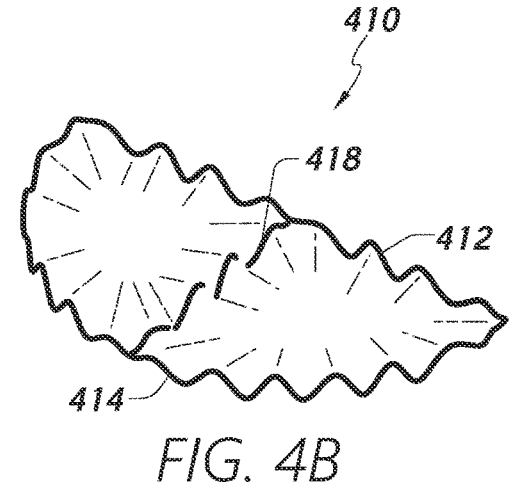
Figure 4C:
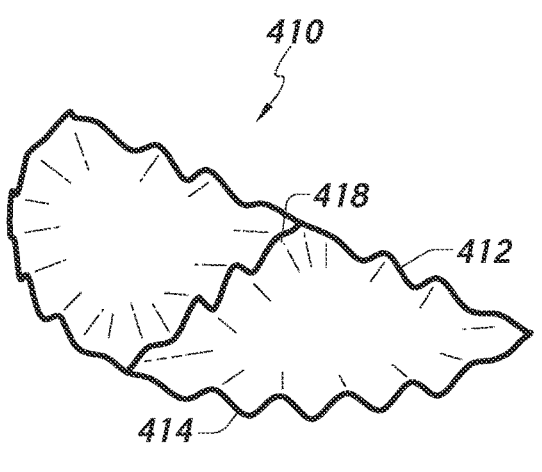
Figure 4D:
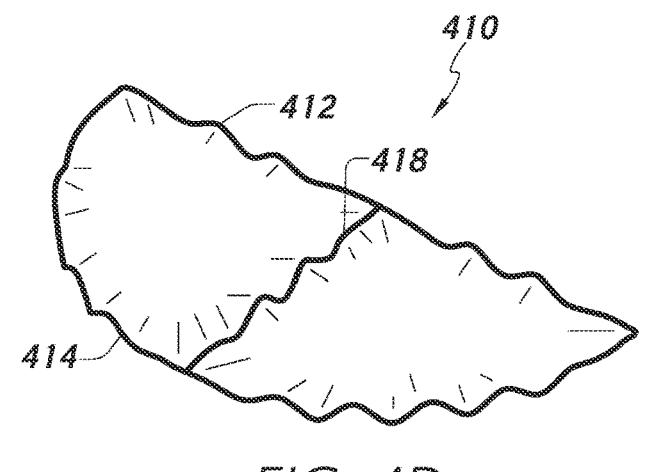
Figure 4E:
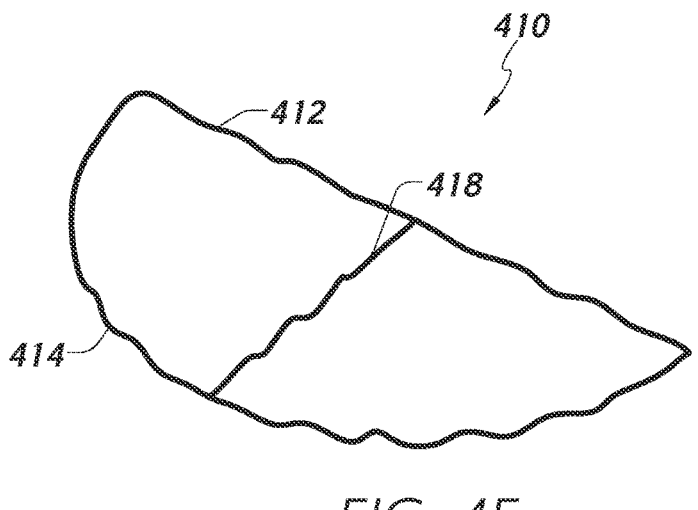

To better illustrate the effect of expansion on a leaflet, FIGS. 4A, 4B, 4C, 4D, and 4E illustrate an example leaflet 410 of a valve as it grows or expands. FIG. 4A illustrates the valve 410 in a compact state or in a squeezed state as it would be in a compact frame implanted in a small patient, such as an infant. As the patient grows, the frame expands which in turn causes the leaflet to expand and flatten in a predictable and targeted fashion. Intermediate sizes of the leaflet 410 are illustrated in FIGS. 4B-4D. The leaflet 410 is illustrated in a fully expanded state in FIG. 4E.

The leaflet 410 includes a coaptation edge 412 configured to interface or interact with a coaptation edge of another leaflet to control the flow of blood through an artificial valve. The coaptation edge 412 is not attached to a frame of the valve and is free to move to allow forward flow of blood and to coapt with another leaflet to restrict or prevent backflow of blood. In some embodiments, the coaptation edge 412 is straight but it is to be understood that the coaptation edge 412 can be any suitable shape or combination of shapes. In some embodiments, the coaptation edge 412 includes a plurality of straight or curved portions configured to be attached run between opposite ends of the peripheral edge 414.

The leaflet 410 includes a peripheral edge 414 that is configured to be attached at a plurality of points to the frame of the valve. Thus, the coaptation edge 412 extends from one end of the peripheral edge 414 to the opposite end of the peripheral edge 414. In some embodiments, the peripheral edge 414 is arcuate in shape but it is to be understood that the peripheral edge 414 can be any suitable shape or combination of shapes. In some embodiments, the peripheral edge 414 includes a plurality of straight or curved portions configured to be attached to a frame or other support structure of the valve.

The leaflet 410 includes a bisecting support 418 that extends from the peripheral edge 414 to the coaptation edge 412. The bisecting support 418 can be configured to extend between the peripheral edge 414 and the coaptation edge 412, as illustrated, or it can be configured to run between portions of the peripheral edge 414, between portions of the coaptation edge 412, between the peripheral edge 414 and another bisecting support (not shown), and/or between the coaptation edge 412 and another bisecting support (not shown). In some embodiments, the bisecting support can extend wholly or partially within the leaflet and not intersect the peripheral edge 414, the coaptation edge 412, and/or another bisecting support (not shown). In some embodiments, the bisecting support 418 can be excluded from the leaflet 410. In certain embodiments, the leaflet 410 can include a plurality of bisecting supports 418.

Each of the coaptation edge 412, the peripheral edge 414, and/or the bisecting support 418 can include a zig zag mesh or wire embedded within or on a surface of the leaflet 410. For example, the mesh or wire can undulate or coil to enable constriction or expansion of the leaflet 410 in response to changes in size of the frame to which the peripheral edge 414 is attached. As shown in the transformation of the leaflet 410 from FIGS. 4A-4E, as the peripheral edge 414 is stretched axially (e.g., points on the peripheral edge are pulled circumferentially apart and away from the coaptation edge 412) a force is also applied to the support structures of the coaptation edge 412 and the bisecting support 418 causing the associated support structures to flatten or uncoil.

This results in a targeted and predictable expansion of the leaflet 410. The targeted and predictable expansion of the leaflet 410 can refer to the leaflet 410 maintaining a targeted shape that allows for the coaptation edge 412 to maintain coaptation with corresponding leaflets of the associated valve. In general, this means that the leaflet 410 is not significantly deformed across the leaflet 410 (e.g., it does not fold over or wrap itself up) and the edges, such as the coaptation edge 412, maintains a targeted shape (e.g., a straight or slightly curved line between opposite ends of the peripheral edge 414). For each of FIGS. 4A-4E, the relatively thicker black lines may represent a wire coupled to the leaflet(s). Such wires can be attached on an outside of the leaflet(s) or can be contained within a channel of the leaflet(s), at least in part. For example, the leaflet(s) can include one or more portions that are folded over and sutured or otherwise attached to the leaflet(s) to form one or more loops or channels through which undulating wire(s) can be inserted.

Figure 5A:
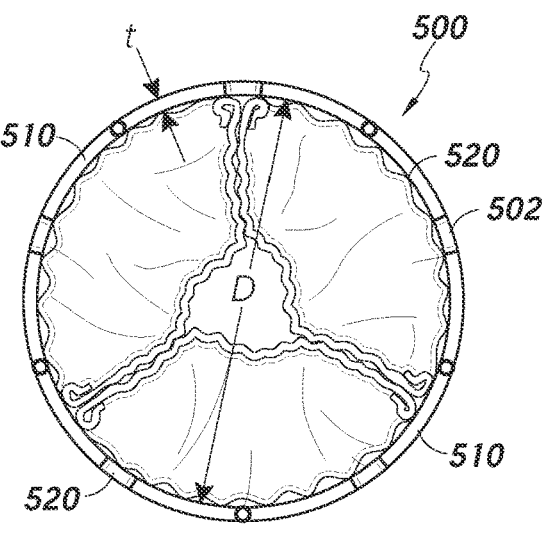
FIG. 5A illustrates an axial view of an example radially self-expanding heart valve device in accordance with one or more embodiments.
Figure 5B:
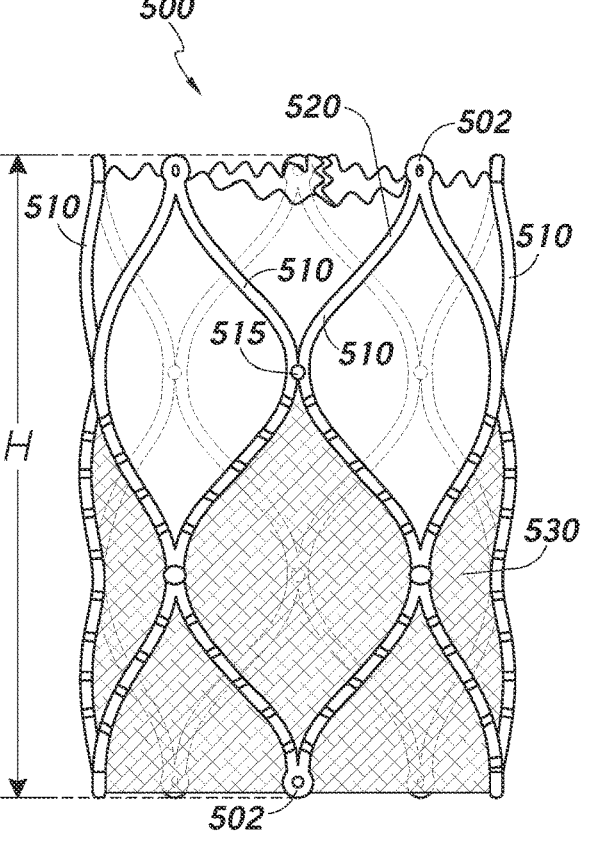
FIGS. 5B and 5C illustrate side views of an example radially self-expanding heart valve device like that shown in FIG. 5A in accordance with one or more embodiments.
Figure 5C:
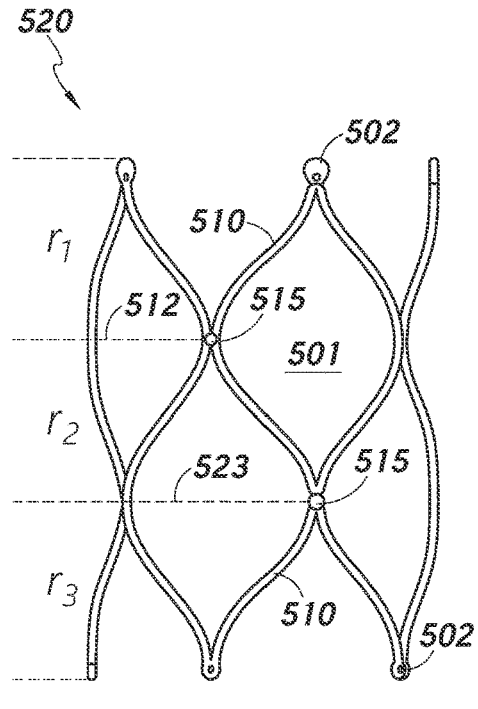

FIGS. 5A-5C illustrate an example of a radially self-expanding valve frame 520 of a self-expanding heart valve device 500 in accordance with aspects of the present disclosure, wherein FIGS. 5A and 5B show the frame 520 as a component of the self-expanding heart valve device 500, whereas FIG. 5C shows only the frame 520 for clarity. In particular, FIGS. 5A-5C illustrate various axial and side views, respectively, of the valve frame 520 in an at least partially expanded state.

The heart valve device 500 (and frame 520) can generally form a tubular structure, as shown in the top view of FIG. 5A. The diameter D of the valve frame 520 can vary from about 5 mm to about 50 mm between a crimped state and an initial expanded state prior to any growth that may occur post-operatively (i.e., "initial expanded state"). As shown in FIG. 5B, the height H of the valve frame 520 can vary from about 14 mm to about 50 mm. Generally, an inverse relationship may exist between the height H and the diameter D and/or the strut spacing as the configuration of the valve frame 520 changes between a compressed/default state and the initial expanded state and/or vice versa.

At each diameter D and corresponding height H, the valve frame 520 can produce a force pointing/directed radially outward from an axis of the valve frame to cause the valve frame 520 to radially expand or grow with expansion of the vessel/anatomy (e.g., aortic valve annulus) in which it is implanted. In some implementations and embodiments, expansion of the valve device 500 after implantation thereof can be caused at least in part by self-expanding characteristics of the valve frame 520 in connection with shape memory of the valve frame 520. For example, the valve frame 520 can comprise memory metal, such as Nitinol, which is a nickel-titanium alloy. Such devices may have a memory shape such that the valve frame advantageously self-deploys relatively gently and/or atraumatically without the need for a deployment balloon to induce the desired expansion. Shape-memory valve frames in accordance with embodiments of the present disclosure can advantageously comprise super-elastic properties. Furthermore, in some embodiments, valve frames in accordance with the present disclosure can be at least partially configured to conform to the shape of the target anatomy in which is it is deployed, such as to the aortic valve annulus and/or aorta, which can be somewhat tortuous in some patients. The valve device 500 can be deployed by retracting a delivery sheath/catheter to expose the valve device in the target vessel, and/or by pushing the valve device distally out of the delivery sheath/catheter.

The valve frame 520 can be configured to expand until it contacts the target anatomy and exerts a continuous outward force, such that any remodeling by, or engagement with, the target anatomy after implantation may be achieved/accommodated by the valve frame 520 through subsequent (e.g., post-operative) expansion thereof. For example, Where the valve frame 520 is at least partially sutured to, embedded in, or otherwise attached/secured to the vessel wall, expansion of the wall due to patient growth may cause expansion of the valve frame.

The valve frame 520 may be tubular and/or annular but may also be provided in other shapes. In addition, the valve frame 520 can be adaptable or pliable such that the cross-sectional and/or axial shape thereof can conform to the shape of the anatomy in which it is implanted. In other words, the shape of the valve frame 520 may depend at least in part on the cross-section shape of the target anatomy/annulus at the implant site.

The valve frame 520 includes a plurality of struts 510 joined by/at joints 515 at proximal and distal ends of the valve frame 520. Each strut 510 is advantageously curved and is joined to an adjacent strut 510 at a corresponding joint 510. For example, the struts 510 can advantageously have an S-curve shape, which may provide characteristics that can be expanded/bent without causing substantial damage to the valve frame/joints. In some embodiments, the joints 515 alternate between proximal and distal ends or relative positions of the valve frame 520, as shown. For example, a first strut 510 can be joined to a second strut 510 at a first joint 515 facing in a proximal direction and a second strut 510 is joined to a third strut 510 at a second joint 515 oriented in a distal direction or relative position of the valve frame 515. This pattern generally repeats to form the tubular structure of the valve frame 520. The joints 515 can be configured to allow the struts 510 to circumferentially expand and contract to produce radial expansion/contraction of the valve frame 520 and can contribute to the radial outward force produced by the valve frame 520.

In some embodiments, the struts 510 can be of the same shape with adjacent struts being vertical (e.g., running from proximal to distal) and/or circumferential reflections of each other. In certain implementations, the struts 510 can have a similar shape as a portion of the graph of the tangent function, or may have any other at least partially curved shape.

For applications relating to interventions for children and infants, who generally have relatively small anatomy (e.g., aortic diameter), it can be desirable or critical for dimensions and features of a valve frame for implantation in such patients to be carefully calculated and/or determined in order to provide the ability to compress to a provide sufficiently small for insertion in relatively small catheters, such as within a 6 or 5 French (Fr) catheter. Although 5 and 6 Fr catheters are disclosed, other-sized catheters are also within the scope of the present disclosure, including catheters smaller than 6 or 5 Fr. Furthermore, the dimensions and features should be selected to present sufficient outward radial force over time to result in post-operative growth of the valve frame that correlates with the growth of the patient, while still being thin enough and/or otherwise configurable to compress within a 6 or 5 Fr catheter. Therefore, embodiments of the present disclosure provide features relating to the number of circumferential struts, the number of axial rows of struts, the thickness of the valve frame struts, the axial height of the valve frame, the circumferential spacing between struts, and/or the like, that advantageously allow for the particular applications for which the respective embodiments are designed. Furthermore, it should be understood that certain dimensions disclosed herein that are designed for particular use in children and infants for whom substantial cardiac growth is expected, and are designed in accordance therewith, are not merely trivial or obvious variants of dimensions of valve frames dimensioned for use in adults and/or other patient for which substantial post-operative vessel growth is not expected, but rather are based on particular combinations of dimensions/features to produce each of the following results: sufficient outward radial self-expansion force to produce post-operation growth expansion, outward radial self-expansion force that is not strong enough to result in propagation/migration of the valve frame through the target vessel wall or other damage to the target anatomy/annulus, and/or axial height sufficient for purposes of valve replacement. Furthermore, where such valve frame is combined with self-growing leaflets, fully self-growing heart valve devices can be produced.

When crimped or in a compact/compressed state (e.g., not fully expanded), the valve frame 520 can produce an outward force based at least in part on the shape and/or thickness of the struts 510. When expanded, the valve frame 520 can resist contraction caused by inward radial forces applied by the vessel in which it is implanted. In some implementations, the outward radial force of the valve frame 520 can be based at least in part on, and/or adjustable at least in part through selection of, the radial thickness t of the struts 510. As an example, where the thickness t of the struts 510 is about 0.33 mm, the range of radial forces produced by the valve frame 520 may be between about 1 N and about 3 N. As another example, where the wall thickness t of the struts 510 is about 0.48 mm, the range of radial forces produced by the valve frame 520 may be between about 5 N and about 5 N. The range of forces can be tuned or tailored by adjusting the wall thickness of the struts 510, for example. In some embodiments, increasing the wall thickness can increase the radial forces produced by the valve frame. Different configurations of strut shape, wall thickness, joints, nodes, strut material, and the like can be arranged to alter/determine the range of radial forces generated by the valve frame 520. The numbers provided herein are merely examples and any other numbers/values may be used within the scope of the present disclosure.

In some embodiments, the wall/radial thickness t of the struts 510 is at least about 0.2 mm and/or less than or equal to about 0.7 mm, at least about 0.25 mm and/or less than or equal to about 0.6 mm, or at least about 0.3 mm and/or less than or equal to about 0.5 mm. In various embodiments, the radial force produced by the valve frame 520 exceeds at least about 0.5 N, exceeds at least about 0.75 N, exceeds at least about 1 N, exceeds at least about 5 N, or exceeds at least about 3 N. Similarly, the radial force produced by the valve frame 520 can be less than or equal to about 10 N, less than or equal to about 8 N, less than or equal to about 6 N, less than or equal to about 5 N, or less than or equal to about 3 N.

The heart valve device can advantageously be configured to be compressed to a profile that is less than or equal to 6 French (e.g., less than or equal to about 5 mm). In the crimped state, the valve frame 520 can experience a maximum principal strain of less than or equal to about 6.27%, or any other percentage. The crimped valve frame 520 can advantageously has a profile that is less than or equal to 5 mm so that it can be implanted percutaneously in certain infant patients, which have relatively small blood vessels compared to older children and adults. In some embodiments, the valve frame 520 is sutured to a cloth skirt 530, which may serve to provide fluid sealing for a portion of the height H of the frame 520, promote tissue ingrowth and/or to increase the surface area of the valve frame and thereby distribute the outward radial force thereof more evenly to prevent the struts of the valve frame from damaging the target anatomy.

Although it is possible to perform minimally-invasive through-chest surgical interventions on young children and infants, due to the relatively fragile physical states of infants with heart-related conditions, interventions requiring general anesthesia may be undesirable or untenable. For example, often infant patients suffering from valve disfunction also suffer from one or more other conditions and/or complications, and so they may not be fit to tolerate non-percutaneous/-transcatheter cardiac surgical interventions. Therefore, embodiments of the present disclosure having the particular ranges of dimensions and/or number/arrangement of struts disclosed can be safer for certain infant patients.

The valve frame 520 can be made of any of various suitable self-expanding materials (e.g., Nitinol) as known in the art. When constructed of a self-expandable/shape-memory material, the valve frame 520 can be crimped to a radially compressed state and restrained in the compressed state by insertion into a sheath or equivalent mechanism/component of a delivery catheter. Once inside the body, the valve device 500 can be advanced from the delivery sheath/catheter, which allows the valve frame 520 to produce radially outward forces to expand and be implanted at the targeted site. The valve frame 520 can be made from shape memory alloys such as nickel titanium (nickel titanium shape memory alloys, or NiTi, as marketed, for example, under the brand name Nitinol), or other biocompatible metals.

The valve frame/device can have a generally annular or toroidal body, which may be formed at least in part from a suitable shape-memory material (e.g., metal, alloy, etc.), such as spring steel, Elgiloy®, or Nitinol. In some embodiments, the material from which the valve frame 520 is fabricated allows the valve frame to automatically, or at least partially automatically, expand from the compressed/crimped state to the expanded state when deployed. In some embodiments, the valve frame 520 is not self-expanding, wherein expansion to the post-operative further-expanded configuration is achievable using another expansion mechanism, such as a balloon catheter.

Generally, the valve frame 520 may have a form or shape defining a number of peaks and valleys (or crests and troughs) along its circumference. For example, the valve frame 520 can have S-shaped sawtooth struts, as shown in FIGS. 5B and 5C, straight sawtooth struts, ringlet-shaped struts, or other-shaped struts forming peaks and valleys. Although the peaks of the valve frame 520 are shown as pointed, in some embodiments, the valve frame 520 has a more curved, generally sinusoidal, side profile, wherein the peaks are rounded curves, or the like.

The valve frame 520 can be sized such that the valve frame 520 can be positioned within the aortic annulus of a patient. In some embodiments, valve frames may have a diameter that is equal to or smaller than the diameter of the relevant prosthetic heart valve when fully expanded. The joint forms/structures 520 of the valve frame 520 can serve as arms that facilitate positioning and/or deployment of the valve frame 520 into the target position in some implementations. For example, the joint forms/structures 520 may have respective apertures 521, which may be used for deployment by arms/fingers of the delivery system.

The thickness t (see, e.g., FIG. 5A) of the frame of a heart valve device in accordance with the present disclosure, such as the valve frame 520, may vary from embodiment to embodiment, but in certain embodiments is between about 0.2-0.3 mm. For example, in a preferred embodiment, the thickness t of the struts 510 is about 0.22 mm, which may provide a suitable balance between outward radial force, strength, and softness/flexibility. For example, a thickness t of about 0.22 mm can produce desirable outward growth-expansion for a valve frame having strut features, dimensions, arrangement, and/or configuration like the valve frame 520 shown in FIGS. 5A-5C.

In some embodiments, valve frames in accordance with the present disclosure are cut from a metal (e.g., memory metal) tube having the desired strut thickness. In certain preferred embodiments, self-growing valve frames comprise and/or are made/cut from Nitinol. In some embodiments, struts of an example self-growing valve frame in accordance with aspects of the present disclosure have a thickness t of about 0.2 mm. In some embodiments, struts of an example self-growing valve frame in accordance with aspects of the present disclosure have a thickness t of about 0.21 mm. In some embodiments, struts of an example self-growing valve frame in accordance with aspects of the present disclosure have a thickness t of about 0.23 mm. In some embodiments, struts of an example self-growing valve frame in accordance with aspects of the present disclosure have a thickness t of about 0.24 mm. In some embodiments, struts of an example self-growing valve frame in accordance with aspects of the present disclosure have a thickness t of about 0.25 mm. The various dimensions disclosed herein in connection with the embodiments of the present disclosure have been determined based on crush tests, radial force tests, and/or other tests/data to determine optimal values and/or ranges of values for dimensions.

Figure 6:
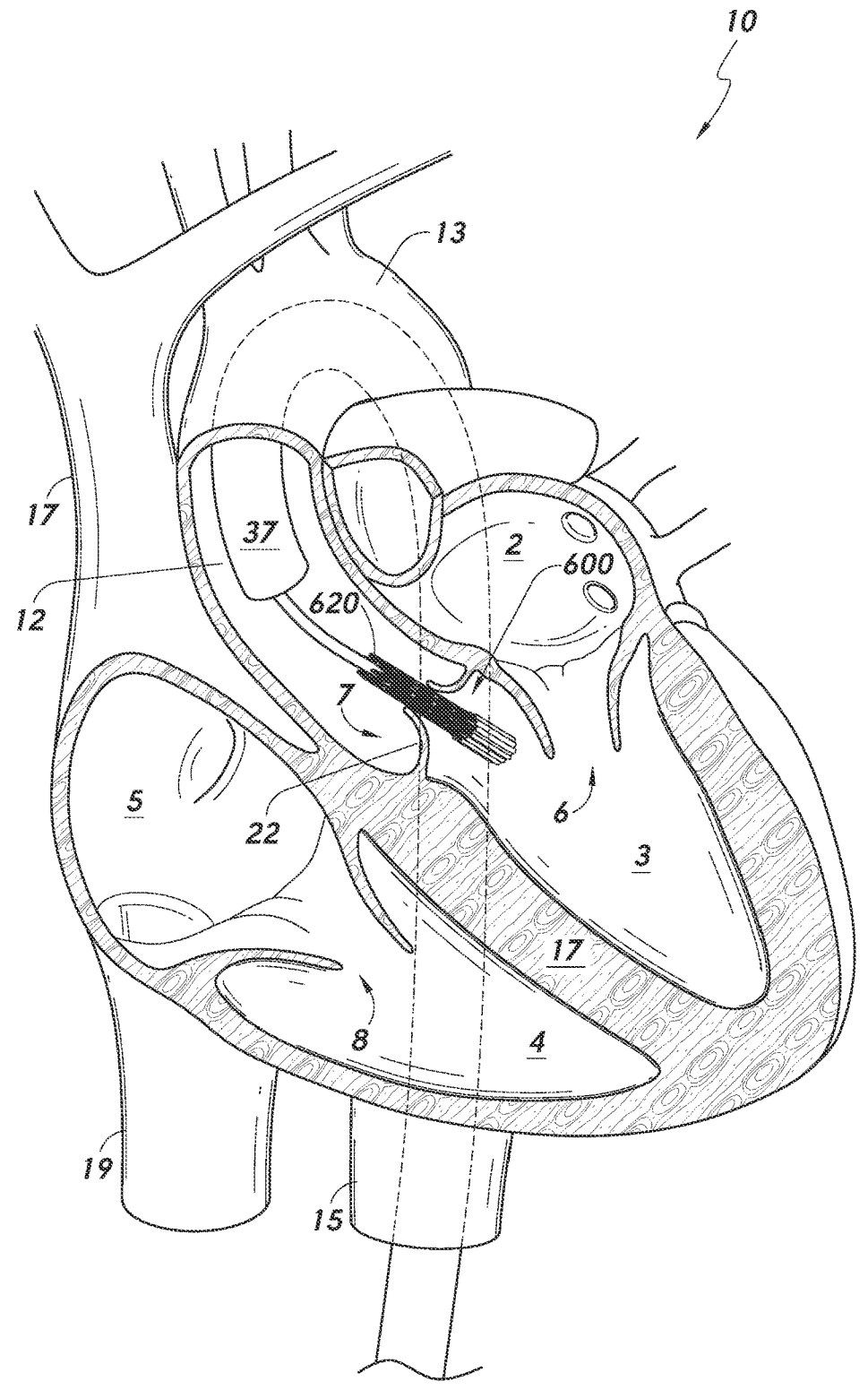
FIG. 6 illustrates a partial cross-sectional view of cardiac anatomy with a delivery system disposed in aortic anatomy thereof.

FIG. 6 illustrates a partial cross-sectional view of cardiac anatomy 10 with a delivery system 37 disposed in aortic anatomy thereof. Rather than accessing the aortic anatomy through an open-chest or other invasive surgical procedure, self-growing prosthetic heart valves in accordance with embodiments of the present disclosure can advantageously be implanted in, for example, children and/or infants using a transcatheter procedure to access an area of a diseased heart valve through the arterial and/or venous system(s). Such procedures can be done through very small openings that leave all the chest bones in place. Furthermore, transcatheter access can result in a relatively faster recovery in most cases. However, transcatheter procedures can present certain challenges for small patients, such as infants and small children. For example, the relatively small arteries and/or veins can be difficult to navigate and can require particularly small catheters, and therefore small implant devices that can fit in such catheters.

As shown in FIG. 6, a delivery catheter 37 may be advanced to a target valve 7 through the aortic anatomy. For example, the catheter 37 may enter through the femoral artery according to a transfemoral approach, which does not require a surgical incision in the chest. As an alternative, the approach to the aorta may be made through the venous system (e.g., femoral vein and/or inferior vena cava), wherein the access path crosses over into the arterial system at or near the abdominal aorta. The delivery catheter 37 may advantageously be a 6 French catheter, or smaller, for navigation in a relatively small vasculature.

With further reference to FIG. 6, in the illustrated crimped state, the valve device 600 can be less than about 5 French. In the crimped state, the valve device 600 can be navigated through narrow passages in the vasculature during positioning of the device, such as within a delivery system sheath/catheter. In some embodiments, the valve frame 620 is configured to provide targeted outward radial forces as it transitions from the crimped state to an initial expanded state, and further to a post-operative expanded state. This can facilitate adequate deployment at the final location in some implementations without requiring the valve frame 620 to first be radially expanded manually. The valve frame 620 is configured to provide operability at a range of sizes/diameters so that the valve frame 520 continues to provide targeted outward radial forces as the vessel expands and/or the patient grows.

Figure 7:
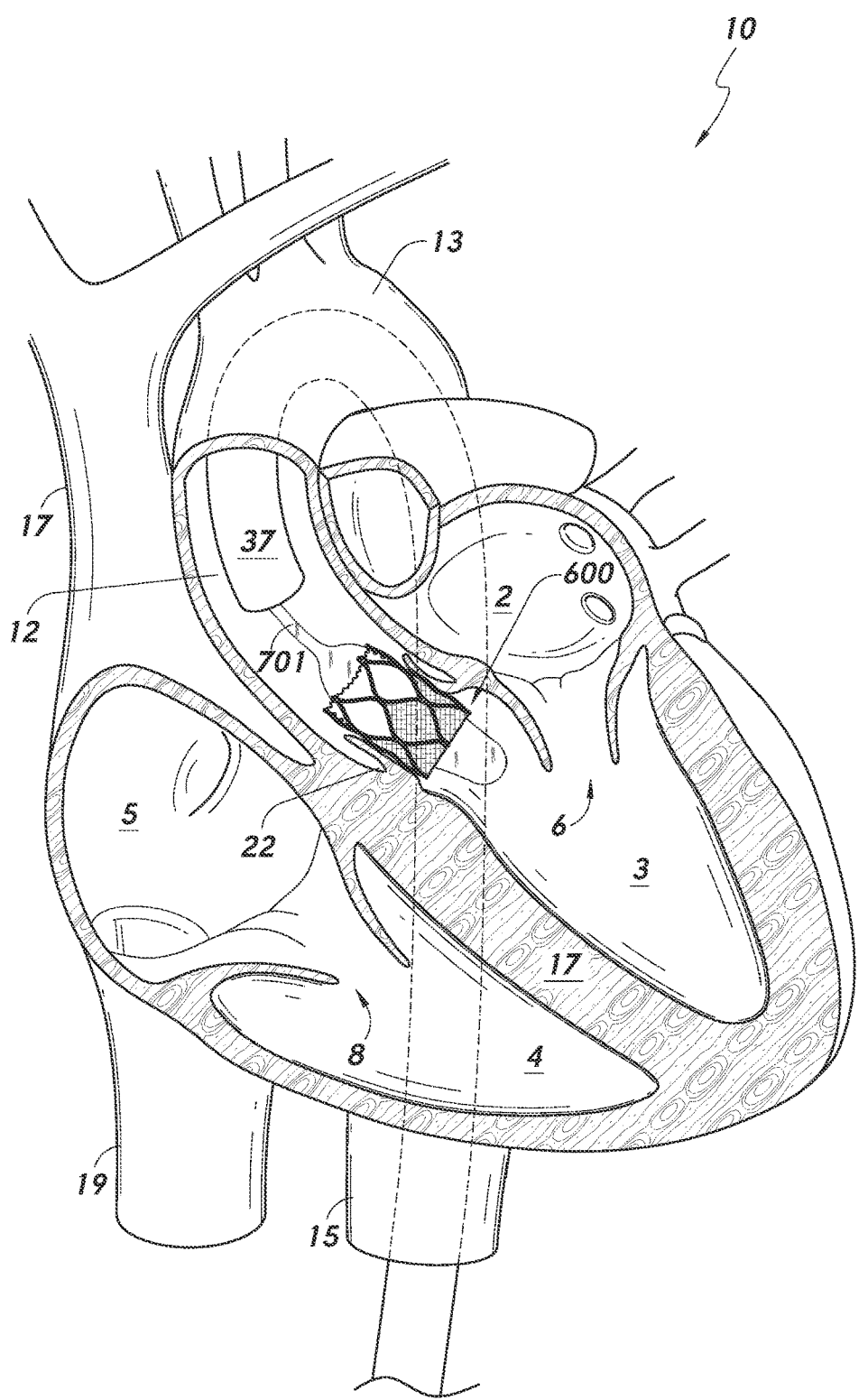
FIG. 7 illustrates the delivery system of FIG. 6 with an expansion mechanism thereof being used to expand a radially self-expanding heart valve device in accordance with one or more embodiments.

In FIG. 6, the valve device 600 is shown deployed from a sheath of the delivery system 37 and positioned within the aortic valve 7. The valve device 600 may initially be deployed in a compressed state, as shown in FIG. 6. FIG. 7 shows expansion of the valve device 600 within the heart valve annulus. For example, the valve device 600 may be expanded using a balloon catheter 701 or may be configured to expand substantially automatically using memory metal characteristics associated with the frame and/or leaflets of the valve device 600.

Figure 8:
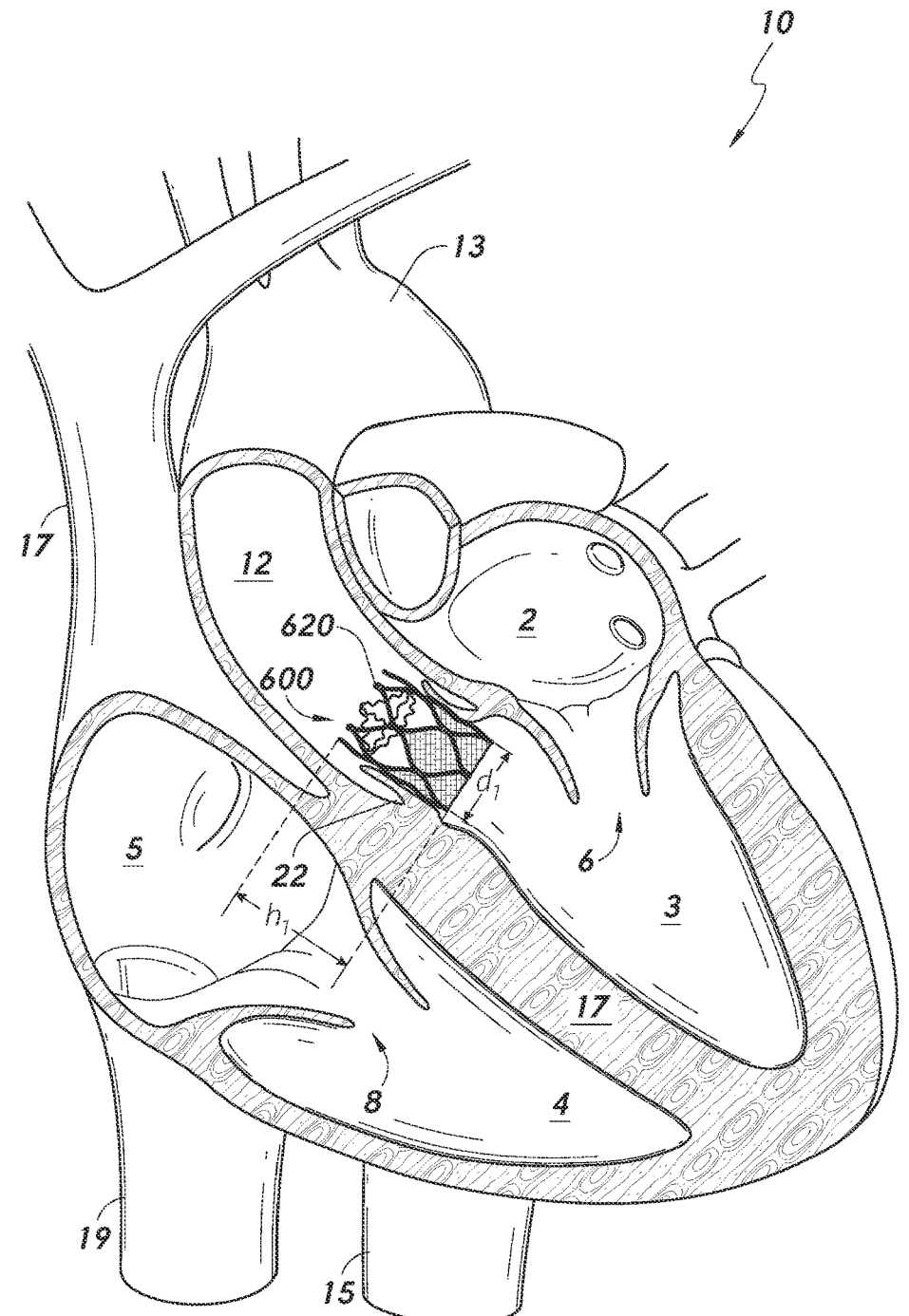
FIG. 8 shows a radially self-expanding heart valve device implanted in cardiac anatomy in an expanded configuration in accordance with one or more embodiments.

FIGS. 8 and 9 show the implanted self-growing valve device 600 at two different sizes, namely an initial expanded state/size and a post-operative growth state/size. In some embodiments, the stent 400 expands from a diameter $D_1$ to a diameter $D_2$, where diameter $D_1$ can be less than or equal to about 5 mm and the diameter $D_2$ can be at least about 50 mm, or any value in between these. For each diameter of the valve device, the frame thereof may be configured to produce an outward radial force. In some embodiments, in addition to the wall thickness of the struts, the radial force of the valve device/frame can depend at least in part on the current diameter of the device 600. For example, as the diameter increases to a maximum operating diameter or post-operative growth expansion diameter, the radial force can decrease. The relationship between the diameter and the radial force can be a function of the wall thickness of the frame struts, the shape of the struts, the joints, the nodes, the material of the struts, and the like. Thus, the relationship between the diameter and the radial force can be a complicated function and need not be monotonically related.

After implantation of the valve device 600, the friction-fit of the device with the aortic wall and/or annulus may be sufficient to maintain the device 600 in the desired position/location. Generally, where too much tissue overgrowth has occurred over the frame of the valve device 600, such tissue growth may undesirably lock the device in its current configuration, thereby preventing the device 600 from growing post-operatively as the patient's anatomy grows. Therefore, although some embodiments can include a sealing skirt/layer comprising cloth, such components can result in undesirable tissue growth. Therefore, in some embodiments, no sealing skirt/cloth is included, at the expense of sacrificing sealing functionality.

In the image of FIG. 9, the self-growing heart valve device 600 is in a partially- or fully-expanded state with a diameter $d_2$ that is greater than the diameter $d_1$ in FIG. 8. That is, the configuration of the heart valve device 600 in FIG. 9 is a post-operative growth-expansion configuration, wherein the device 600 has a diameter $d_2$ greater than that of the device 600 at or soon after implantation thereof, wherein such diameter expansion is produced or effected at least in part by outward radial force exerted inherently by the shape memory characteristics of the valve device 600 and/or fixation to the surrounding anatomy that undergoes diametrical growth over a post-operative/implantation period of time. For example, the configuration of the device 600 in FIG. 9 may represent a post-implantation-expansion state a period of time after implantation in which the diameter of the device 600 has increased without requiring a post-implantation intervention to achieve or effect such expansion.

With reference to FIGS. 8 and 9, the diameter $d_1$ may be about 10 mm, or any value between about 10-14 mm. In some embodiments, the diameter $d_1$ is about 9 mm, or another value between about 5 mm and 10 mm. In some embodiments, the diameter $d_1$ is about 3 mm. In some embodiments, the diameter $d_1$ is about 4 mm. In some embodiments, the diameter $d_1$ is about 5 mm. In some embodiments, the diameter $d_1$ is about 6 mm. In some embodiments, the diameter $d_1$ is about 7 mm. In some embodiments, the diameter $d_1$ is about 8 mm.

The growth-expansion diameter $d_2$ may be about 50 mm, or any value between 14-50 mm. In some embodiments, the diameter $d_2$ is about 14 mm. In some embodiments, the diameter $d_2$ is about 15 mm. In some embodiments, the diameter $d_2$ is about 16 mm. In some embodiments, the diameter $d_2$ is about 17 mm. In some embodiments, the diameter $d_2$ is about 18 mm. In some embodiments, the diameter $d_2$ is about 19 mm. In some embodiments, the diameter $d_2$ is between about 50-55 mm. In some embodiments, the diameter $d_2$ is greater than about 55 mm. In some embodiments, the diameter $d_2$ is about 55 mm.

Due to the bending and expansion of the struts of the valve frame 620 in connection with expansion from the diameter $d_1$ to the diameter $d_2$, the height of the valve 600 and/or valve frame 620 may be reduced from the deployed height $h_1$ to the post-operative growth height $h_2$ shown in FIG. 9. Generally, the height $h_2$ of the valve/frame in the growth-expansion state may be less than the height $h_1$ in the initial expanded state.

The growth expansion of the self-growing heart valve device 600 may be due at least in part to substantially constant radial force exerted by the valve frame 620 due to shape memory characteristics thereof, as described in detail herein. Furthermore, in some implementations, the struts of the valve frame 620 may become overgrown by endothelial tissue growth over time after implantation of the valve device 600. Such tissue growth may serve to at least partially secure the valve device 600 to the vessel wall and/or valve annulus, which may further exert outward radial force on the valve device 600 as the patient grows, thereby causing expansion in the valve device post-operatively based on the particular strut dimensions, configuration, and arrangement of the valve device 600. In some embodiments, the valve frame 620 is configured to present an optimum outward radial force that it is sufficient to at least partially break or disrupt endothelial tissue overgrowth to a degree that the tissue overgrowth does not prevent further post-operative expansion of the device caused by the shape memory characteristics thereof, at least for an initial post-operative phase (e.g., about 90 days).

FIG. 10 illustrates a flow chart of an example process 100 for treating heart valve disease with any of the self-growing heart valve devices described herein. The process 100 can be used to treat any patient with a defective heart valve but may be particularly suitable for patients weighing less than about 10 kg. The implanted valve device may be particularly advantageous for this class of patients due at least in part to the valve being configured to operate at relatively small compressed diameters (e.g., about 2 mm) and to the valve device being configured to continue to operate as the target anatomy (e.g., aortic valve annulus) increases in size.

At block 101, the process 100 involves providing a self-growing heart valve device in accordance with one or more embodiments of the present disclosure. For example, the valve device may have any configuration described herein with respect to the expandable mechanism/feature associated with the heart valve leaflets and/or the number of axial rows of struts, struct thickness, material, strut shape, valve device height, outward radial force, and/or maximum valve device diameter associated with the heart valve frame.

At block 102, the process 100 involves crimping or otherwise compressing the valve device into a low-profile configuration. Crimping/compressing the valve device may involve compressing the valve device to a profile that is less than or equal to about 2 mm in order to fit within a catheter designed for a child's and/or infant's vasculature.

At block 103, the process 100 involves disposing the crimped/compressed valve device in a delivery catheter. The compressed valve device may be maintained in the delivery catheter in any suitable or desirable way. Example delivery systems and/or configurations are shown in FIGS. 6 and 7, which are described above.

At block 104, the process 100 involves delivering the self-growing valve device in the crimped/compressed state through vasculature of the patient in the delivery system. The valve device can be constrained at a reduced diameter (e.g., less than or equal to about 5 or 6 French) by a sheath, catheter or other similar structure of the delivery system.

At block 105, the process 100 involves deploying the valve device at least in part by removing the catheter/sheath. Removing the catheter/sheath allows the valve device to begin to self-expand to an increased diameter. Removal of the catheter/sheath may be facilitated by a pusher, balloon catheter, or other device associated with the delivery system. The valve device can be configured to expand to contact the inner walls of the target valve annulus or other anatomy.

At block 106, the valve device is released to allow the radial self-expansion of the valve device to begin to grow/expand with the growth/expansion of the target anatomy. Advantageously, the method 100 can be used with a pediatric patient and, due at least in part to the structure of the valve device causing radially outward forces over a range of diameters, another valve device may not need to be implanted to replace the device, for example, as the patient grows.

FIGS. 11A and 11B show perspective views of a self-growing heart valve device 1100 in partially- and fully-expanded states, respectively, in accordance with one or more embodiments of the present disclosure. Specifically, FIG. 11A shows the valve device 1100 in a partially-expanded, deployed configuration, whereas FIG. 11B shows the device 1100 in a further- or fully-expanded configuration. The valve 1100 is configured to be operable between the partially-expanded state and the further-expanded state by employing leaflets 1110 that are relatively long, such that the leaflets have an extended coaptation overlap 1111 when the frame 1120 is not fully expanded, wherein the overlapping portion 1111 decreases as the valve device 1100 grows. The leaflets 1110 may not include undulating wire or other components without metal in them, as described in detail above. Therefore, the embodiment of FIGS. 11A and 11B may advantageously have less rigid structure than certain other embodiments.

As the frame 1120 grows, the leaflets 1110 can continuously coapt as the coaptation overlap 1111 decreases. In some embodiments, when the device 1100 is fully expanded, as in FIG. 11B, the edges of the leaflets 1110 may coapt such that there is little or no overlap of the leaflets in the closed state. Aside from the relatively long leaflets 1110, the valve device 1100 may have any suitable or desirable combination of features described above with respect to one or more other embodiments of the present disclosure. Furthermore, although the device 1100 is shown as having three valve leaflets, it should be understood that the device 1100, as with other embodiments of the present disclosure, may have any suitable or desirable number of valve leaflets, such as two leaflets. The overlap 1111 of the leaflets 1110 may advantageously be great enough to provide coaptation of the leaflets 1110 for every device/frame diameter described herein in connection with any of the embodiments of the present disclosure.

The self-growing leaflets 1110 can be dimensioned such that in a partially-expanded state, as in FIG. 11A, the leaflets coapt to a greater degree than in a fully-expanded state, as in FIG. 11B. That is, the leaflets may come together into closer proximity in the partially-expanded state than in the fully-expanded state. For example, in the partially-expanded state, the leaflets may collide or otherwise contact each other in a manner that causes the coaptation edges thereof to fold or project axially with respect to the axis of the heart valve device 1100 (e.g., upward, as shown, with respect to the orientation of FIG. 11A, which may be considered the outflow direction of the valve device 1100). Such folding/projection may be necessitated and/or caused by the dimensions of the leaflets in the direction of adjacent/coapting leaflets being greater than the space/distance between the base of the leaflets and the relevant coaptation area. Such folding/projection may be to a greater degree/distance with respect to the partially-expanded state than for the fully expanded state. In some embodiments, the leaflets do not project/overlap more than a nominal amount in the fully-expanded state.

In certain alternative embodiments, the excess length/dimension of the leaflets can cause the leaflets to radially overlap one another in the partially-expanded state, and to a greater degree with respect to the partially-expanded state/configuration than for the fully-expanded state. The leaflets 1110 can advantageously dimensioned to coapt over a range of diameters of the tubular frame 1120.

Additional Embodiments and Terminology

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional subcomponents to be performed separately. In some instances, the order of the steps and/or phases can be rearranged, and certain steps and/or phases may be omitted entirely. Also, the methods described herein are to be understood to be openended, such that additional steps and/or phases to those shown and described herein can also be performed.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A method of treating a defective heart valve, the method comprising:

advancing a delivery catheter to a target heart valve of a patient;

deploying a self-growing heart valve device from the delivery catheter within an annulus of the target heart valve, the heart valve device including a self-growing tubular frame and a plurality of self-growing leaflets coupled to the self-growing frame;

permitting the self-growing heart valve device to expand within the annulus to thereby implant the heart valve device;

withdrawing the delivery catheter from the patient; and maintaining the self-growing heart valve device within the annulus to thereby allow the self-growing tubular frame and the plurality of self-growing leaflets to grow along with the annulus of the target heart valve.

2. The method of claim 1, wherein said permitting the self-growing heart valve involves expanding the self-growing heart valve with a balloon.

3. The method of claim 1, wherein the plurality of self-growing leaflets include undulated wires.

4. The method of claim 1, wherein the plurality of self-growing leaflets are dimensioned such that in a partially-expanded state, the leaflets coapt to a greater degree than in a fully-expanded state.

5. A method of treating a defective heart valve, the method comprising:

delivering a self-growing heart valve device to a target heart valve of a patient, the self-growing heart valve device including a self-growing frame and a plurality of self-growing leaflets coupled to the self-growing frame, the self-growing frame configured to change in diameter after implantation to accommodate growth of the patient, the plurality of self-growing leaflets configured to increase in size with an increase in size of the diameter of the self-growing frame such that the plurality of self-growing leaflets are adapted to coapt in a range of diameters of the self-growing frame, the range of diameters extending from an initial expanded state to a post-operative expanded state; and deploying the self-growing heart valve device within an annulus of the target heart valve such that the self-growing frame is expanded to the initial expanded state and attached to the annulus; and expanding the self-growing heart valve device to a post-operative expanded state, expansion of the self-growing heart valve due to growth of the patient that causes the annulus to increase in size, wherein the diameter of the self-growing frame in the initial expanded state is less than 14 mm, wherein the diameter of the self-growing frame in the post-operative expanded state is greater than 50 mm, wherein the plurality of self-growing leaflets each include a structural support that provides structure to the plurality of self-growing leaflets at a range of sizes that covers the range of diameters from the initial expanded state to the post-operative expanded state, wherein expansion of the self-growing frame causes points along a peripheral edge of each leaflet of the plurality of self-growing leaflets to be pulled apart axially to expand the structural support along coaptation edges of each leaflet of the plurality of self-growing leaflets such that the plurality of self-growing leaflets coapt in the range of diameters of the self-growing frame from the initial expanded state to the post-operative expanded state.

6. The method of claim 5 further comprising crimping the self-growing frame to a crimped state prior to delivering the self-growing heart valve device.

7. The method of claim 6 further comprising inserting the self-growing heart valve device into a sheath of a delivery device to restrain the self-growing heart valve device in the crimped state.

8. The method of claim 7 further comprising advancing the self-growing heart valve device from the sheath to allow the self-growing tubular frame to produce the radially outward force to be implanted at the target heart valve.

9. The method of claim 5, wherein the structural support comprises undulated wires.

10. The method of claim 5, wherein expansion of the annulus due to patient growth radially expands the self-growing frame and expands a peripheral edge and a coaptation edge of each of the plurality of self-growing leaflets.

11. The method of claim 5, wherein the self-growing frame is adapted to exert a radially outward force in each state between the initial expanded state and the post-operative expanded state.

12. The method of claim 5, wherein expansion of the self-growing heart valve device from the initial expanded state to the post-operative expanded state includes radial expansion and longitudinal contraction of the self-growing frame.

13. The method of claim 5, wherein the self-growing frame is adapted to conform to a shape of the target heart valve.

14. The method of claim 5, wherein the structural support is along a peripheral edge and a coaptation edge of each of the plurality of self-growing leaflets.

15. A method of treating a defective heart valve, the method comprising:

compressing a self-growing heart valve device to a low-profile configuration, the self-growing heart valve being in a crimped state in the low-profile configuration, the self-growing heart valve device including a self-growing frame and a plurality of self-growing leaflets coupled to the self-growing frame;

delivering the self-growing heart valve device in the crimped state to a target heart valve of a patient; and deploying the self-growing heart valve device within an annulus of the target heart valve, the self-growing heart valve adapted to expand to an initial expanded state such that the self-growing frame exerts a radially outward force against the annulus of the target valve to implant the self-growing heart valve device at the target heart valve, wherein, after deployment, the self-growing frame exerts a radially outward force such that the self-growing heart valve device is adapted to expand from the initial expanded state to a post-operative expanded state to accommodate growth of the annulus of the target heart valve due to growth of the patient, wherein the plurality of self-growing leaflets is adapted to continue to coapt with expansion of the self-growing heart valve from the initial expanded state to the post-operative expanded state.

16. The method of claim 15 further comprising compressing the self-growing heart valve device to a low-profile configuration that is less than or equal to 2 mm in diameter to fit within a catheter designed for vasculature of a child.

17. The method of claim 15 further comprising using transcatheter access to implant the self-growing heart valve device in an infant or child.

18. The method of claim 17, wherein, in the crimped state, the self-growing heart valve device is less than 5 French.

19. The method of claim 15, wherein a diameter of the self-growing frame in the initial expanded state is between about 10 mm and 14 mm.

20. The method of claim 15, wherein the diameter of the self-growing frame in the post-operative expanded state is between 14 mm and 50 mm.

\* \* \* \* \*